(12) United States Patent
Arbeit

(10) Patent No.: US 6,838,430 B2
(45) Date of Patent: Jan. 4, 2005

(54) USE OF HIF-1A VARIANTS TO ACCELERATE WOUND HEALING

(75) Inventor: Jefferey M. Arbeit, San Francisco, CA (US)

(73) Assignee: The Regents of the University of California, Oakland, CA (US)

(*) Notice: Subject to any disclaimer, the term of this patent is extended or adjusted under 35 U.S.C. 154(b) by 342 days.

(21) Appl. No.: 09/967,388

(22) Filed: Sep. 28, 2001

(65) Prior Publication Data

US 2003/0103956 A1 Jun. 5, 2003

(51) Int. Cl.$^7$ .............................................. C07K 14/00
(52) U.S. Cl. .......................................... 514/2; 530/350
(58) Field of Search ............................... 514/2; 530/350

(56) References Cited

U.S. PATENT DOCUMENTS

| | | | | |
|---|---|---|---|---|
| 5,604,293 A | * | 2/1997 | Fiddes et al. | ............... 530/399 |
| 5,882,914 A | | 3/1999 | Semenza | ................. 435/252.3 |
| 6,124,131 A | | 9/2000 | Semenza | .................... 435/325 |
| 6,562,799 B1 | * | 5/2003 | Semenza | ..................... 514/44 |

OTHER PUBLICATIONS

Arbeit, J. M. et al., "Progressive squamous epithelial neoplasta In K14–human papillomavirus type 16 transgenic mice," *Journal of Virology*, vol. 68, No. 7, pp. 4358–4368 (1994).

Arbeit, J. M. et al., "Unpregulation of fibroblast growth factors and their receptors during multi–stage epidermal carcinogenesis in K14–HPV16 transgenic mice," *Oncogene*, vol. 13, pp. 1847–1857 (1996).

Arbeit, J. M., "Transgenic models of epidermal neoplasta and multi–stage carcinogenesis," *Cancer Surveys*, vol. 26, pp. 7–34 (1986).

Cardiology Network (Headlines): Sep. 26, 2001 8:07:24 PM, "Gene Therapy for Blood Vessel Growth to be Tested at University of Pittsburgh Medical Center," World Wide Web Address: headlines.cardiologynet.org: pp. 1–2.

Carmeliet, P. et al., "Angiogenesis in cancer and other diseases," *Nature Cell Biology*, vol. 407, pp. 249–257 (2000).

Detmar, M. et al., "Increased Microvascular Density and Enhanced Leukocyte Rolling and Adhesion in the Skin of VEGF Transgenic Mice," *The Journal of Investigative Dermatology*, vol. 111, pp. 1–6 (1998).

Elson, D. A. et al., "Coordinate up–regulation of hypoxia inducible factor (HIF)–1α and HIF–1 target genes during multi–stage epidermal carcinogenesis and wound healing," *Cancer Research*, vol. 60, pp. 6189–6195 (2000).

Feldser, D. et al., "Reciprocal positive regulation of hypoxia–inducible factor 1α and insulin–like growth factor 2," *Cancer Research*, vol. 59, pp. 3915–3918 (1999).

Forsythe, J. A. et al., "Activation of Vascular Endothelial Growth Factor Gene Transcription by Hypoxia–Inducible Factor 1," *Molecular and Cellular Biology*, vol. 16, No. 9, pp. 4604–4613 (1996).

Huang, L. E. et al., "Regulation and hypoxide–inducible factor 1α is mediated by an $O_2$–dependent degradation domain via the ubiquitin–proteasome pathway," *Proceedings of the National Academy of Sciences of the Unites States of America*, vol. 95, pp. 7987–7992 (1998).

Iyer, N. V. et al., "Cellular and developmental control of $O_2$ homeostasis by hpoxia–inducible factor 1α," *Genes and Development*, vol. 12, pp. 149–162 (1998).

Jettsch, M. et al., "Hyperplasia of Lympathic Vessels in VEGF–C Transgenic Mice," *Science*, vol. 278, pp. 1423–1425 (1997).

Jiang B. H. et al., Dimerization, DNA binding, and transactivation properties of hypoxia–inducible factor 1. *The Journal of Biolgical Chemistry*, vol. 271, No. 30, pp. 17771–17778 (1996).

Jiang, B. H. et al., "Hypoxia–inducible factor 1 levels vary exponentially over a physiologically relevant range of $O_2$ tension," *The American Journal of Physiology*, vol. 271, pp. C1172–1180 (1996).

Jiang, B. H. et al., "Transactivation and Inhibitory Domains of Hypoxie–Inducible Factor 1α," *The Journal of Biological Chemistry*, vol. 272, No. 31, pp. 19253–19280 (1997).

Kallio, P. J. et al., "Regulation of the Hypoxia–inducible Transcription Factor 1α by the Ubiquitin–Proteasome Pathway," *The Journal of Biological Chemistry*, vol. 274, No. 10, pp. 6519–6525 (1999).

Larcher, F. et al., "VEGF/VPF overexpression in skin of transgenic mice induces angiogenesis, vascular hyperpermeability and accelerated tumor development," *Oncogene*, vol. 17, pp. 303–311 (1998).

Lee, S. H. et al., "Early expression of angiogenesis factors in acute myocardial ischemia and infarction," *The New England Journal of Medicine*, vol. 342, No. 9, pp. 626–633 (2000).

Li, J. et al., "PR39, a peptide regulator of angiogenesis," *Nature Medicine*, vol. 6, pp. 49–55 (2000).

Munz, B. et al., Overexpression of activin A in the skin of transgenic mice reveals new activities of activin in epidermal morphogenesis, dermal fibrosis and wound repair, *The Embo Journal*, vol. 18, No. 19, pp. 5205–5215 (1999).

(List continued on next page.)

*Primary Examiner*—Karen Cochrane Carlson
(74) *Attorney, Agent, or Firm*—Ginger R. Dreger; James A. Fox; Heller Ehrman White & McAuliffe LLP

(57) ABSTRACT

The present invention concerns the use of stable HIF-1α variants to accelerate wound healing. More particularly, the present invention provides a method of accelerating wound healing in a mammal comprising administering a stable variant of an HIF-1α polypeptide comprising an oxygen-dependent degradation domain. The stable HIF-1α variant preferably comprises an insertion, deletion or substitution in the oxygen-dependent degradation domain.

24 Claims, 11 Drawing Sheets

OTHER PUBLICATIONS

Ratcliffe, P. J. et al., "Oxygen sensing, hypoxia–inducible factor–1 and the regulation of mammalian gene expression," *The Journal of Experimental Biology*, vol. 201, pp. 1153–1162 (1998).

Ryan, H. E. et al., "HIF–1α is required for solid tumor formation and embryonic vascularization," *EMBO Journal*, vol. 17, No. 11, pp. 3005–3015 (1998).

Semenza, G. L. et al., "Structural and functional analysis of hypoxia–inducible factor 1," *Kidney International*, vol. 51, pp. 553–555 (1997).

Semenza, G. L. et al., "Transcriptional Regulation of Genes Encoding Glycolytic Enzymes by Hypoxia–inducible Factor 1," *The Journal of Biological Chemistry*, vol. 289, No. 38, pp. 23757–23783 (1994).

Semenza, G. L., "Regulation of mammalian $O_2$ homeostasis by hypoxia–inducible factor 1," *Annual Review Cell and Development Biology*, vol. 15, pp. 551–578 (1999).

Thurston, G. et al., "Leakage–Resistant Blood Vessels in Mice Transgenically Overexpressing Angiopoietin –1," *Science*, vol. 288, pp. 2511–2514 (1999).

Vassar, R. et al., "Transgenic mice provide new insights into the role of TGF–α during epidermal development and differentiation," *Genes & Development*, vol. 5, pp. 714–727 (1991).

Vincent, K. A. et al., "Angiogenesis is induced in a rabbit model of hindlimb ischemia by naked DNA encoding an HIF–1α/VP16 hybid transcription factor," *Circulation*, vol. 102, pp. 2255–2261 (2000).

Wang, G. L. et al., "Hypoxia–inducible factor 1 is a basic–helix–loop–helix–PAS heterodimer regulated by cellular $O_2$ tension," *Proc. Natl. Acad. Sci. USA*, vol. 92, pp. 5510–5514 (1995).

Wenger, R. H., "Mammalian oxygen sensing, signalling and gene regulation," *The Journal of Experimental Biology*, vol. 203, pp. 1253–1263 (2000).

Zhong, H. et al., "Increased expression of hypoxia inducible factor–1α in rat and human prostate cancer," *Cancer Research*, vol. 58, pp. 5280–5284 (1998).

\* cited by examiner hHIF1α ΔODD Nucleotide Sequence:

ATGGAGGGCGCCGGCGGCGCGAACGACAAGAAAAAGATAAGTTCTGAACGTCGAAAAGA
AAAGTCTCGAGATGCAGCCAGATCTCGGCGAAGTAAAGAATCTGAAGTTTTTATGAGC
TTGCTCATCAGTTGCCACTTCCACATAATGTGAGTTCGCATCTTGATAAGGCCTCTGTG
ATGAGGCTTACCATCAGCTATTTGCGTGTGAGGAAACTTCTGGATGCTGGTGATTTGGA
TATTGAAGATGACATGAAAGCACAGATGAATTGCTTTTATTTGAAAGCCTTGGATGGTT
TTGTTATGGTTCTCACAGATGATGGTGACATGATTTACATTTCTGATAATGTGAACAAA
TACATGGGATTAACTCAGTTTGAACTAACTGGACACAGTGTGTTTGATTTACTCATCC
ATGTGACCATGAGGAAATGAGAGAAATGCTTACACACAGAAATGGCCTTGTGAAAAAGG
GTAAAGAACAAAACACACAGCGAAGCTTTTTTCTCAGAATGAAGTGTACCCTAACTAGC
CGAGGAAGAACTATGAACATAAAGTCTGCAACATGGAAGGTATTGCACTGCACAGGCCA
CATTCACGTATATGATACCAACAGTAACCAACCTCAGTGTGGGTATAAGAAACCACCTA
TGACCTGCTTGGTGCTGATTTGTGAACCCATTCCTCACCCATCAAATATTGAAATTCCT
TTAGATAGCAAGACTTTCCTCAGTCGACACAGCCTGGATATGAAATTTTCTTATTGTGA
TGAAAGAATTACCGAATTGATGGGATATGAGCCAGAAGAACTTTTAGGCCGCTCAATTT
ATGAATATTATCATGCTTTGGACTCTGATCATCTGACCAAAACTCATCATGATATGTTT
ACTAAAGGACAAGTCACCACAGGACAGTACAGGATGCTTGCCAAAAGAGGTGGATATGT
CTGGGTTGAAACTCAAGCAACTGTCATATATAACACCAAGAATTCTCAACCACAGTGCA
TTGTATGTGTGAATTACGTTGTGAGTGGTATTATTCAGCACGACTTGATTTTCTCCCTT
CAACAAACAGAATGTGTCCTTAAACCGGTTGAATCTTCAGATATGAAAATGACTCAGCT
ATTCACCAAAGTTGAATCAGAAGATACAAGTAGCCTCTTTGACAAACTTAAGAAGGAAC
CTGATGCTTTAACTTTGCTGCAGACTCAAATACAAGAACCTACTGCTAATGCCACCACT
ACCACTGCCACCACTGATGAATTAAAAACAGTGACAAAAGACCGTATGGAAGACATTAA
AATATTGATTGCATCTCCATCTCCTACCCACATACATAAAGAAACTACTAGTGCCACAT
CATCACCATATAGAGATACTCAAAGTCGGACAGCCTCACCAAACAGAGCAGGAAAAGGA
GTCATAGAACAGACAGAAAAATCTCATCCAAGAAGCCCTAACGTGTTATCTGTCGCTTT
GAGTCAAAGAACTACAGTTCCTGAGGAAGAACTAAATCCAAAGATACTAGCTTTGCAGA
ATGCTCAGAGAAAGCGAAAAATGGAACATGATGGTTCACTTTTTCAAGCAGTAGGAATT
GGAACATTATTACAGCAGCCAGACGATCATGCAGCTACTACATCACTTTCTTGGAAACG
TGTAAAAGGATGCAAATCTAGTGAACAGAATGGAATGGAGCAAAAGACAATTATTTTAA
TACCCTCTGATTTAGCATGTAGACTGCTGGGGCAATCAATGGATGAAAGTGGATTACCA
CAGCTGACCAGTTATGATTGTGAAGTTAATGCTCCTATACAAGGCAGCAGAAACCTACT
GCAGGGTGAAGAATTACTCAGAGCTTTGGATCAAGTTAAC

FIG. 6 hHIF1α ΔODD Protein Sequence:

MEGAGGANDKKKISSERRKEKSRDAARSRRSKESEVFYELAHQLPLPHNVS
SHLDKASVMRLTISYLRVRKLLDAGDLDIEDDMKAQMNCFYLKALDGFVMV
LTDDGDMIYISDNVNKYMGLTQFELTGHSVFDFTHPCDHEEMREMLTHRNG
LVKKGKEQNTQRSFFLRMKCTLTSRGRTMNIKSATWKVLHCTGHIHVYDTN
SNQPQCGYKKPPMTCLVLICEPIPHPSNIEIPLDSKTFLSRHSLDMKFSYC
DERITELMGYEPEELLGRSIYEYYHALDSDHLTKTHHDMFTKGQVTTGQYR
MLAKRGGYVWVETQATVIYNTKNSQPQCIVCVNYVVSGIIQHDLIFSLQQT
ECVLKPVESSDMKMTQLFTKVESEDTSSLFDKLKKEPDALTLLQTQIQEPT
ANATTTTATTDELKTVTKDRMEDIKILIASPSPTHIHKETTSATSSPYRDT
QSRTASPNRAGKGVIEQTEKSHPRSPNVLSVALSQRTTVPEEELNPKILAL
QNAQRKRKMEHDGSLFQAVGIGTLLQQPDDHAATTSLSWKRVKGCKSSEQN
GMEQKTIILIPSDLACRLLGQSMDESGLPQLTSYDCEVNAPIQGSRNLLQG
EELLRALDQVN

FIG. 7

```
GTGAAGACATCGCGGGGACCGATTCACCATGGAGGGCGCCGGCGGCGCGAAGACAAGAA
CGACAAGAAAAAGATAAGTTCTGAACGTCGAAAAGAAAAGTCTCGAGATGCAGCCAGAT
CTCGGCGAAGTAAAGAATCTGAAGTTTTTTATGAGCTTGCTCATCAGTTGCCACTTCCA
CATAATGTGAGTTCGCATCTTGATAAGGCCTCTGTGATGAGGCTTACCATCAGCTATTT
GCGTGTGAGGAAACTTCTGGATGCTGGTGATTTGGATATTGAAGATGACATGAAAGCAC
AGATGAATTGCTTTTATTTGAAAGCCTTGGATGGTTTTGTTATGGTTCTACAGATGAT
GGTGACATGATTTACATTTCTGATAATGTGAACAAATACATGGGATTAACTCAGTTTGA
ACTAACTGGACACAGTGTGTTTGATTTTACTCATCCATGTGACCATGAGGAAATGAGAG
AAATGCTTACACACAGAAATGGCCTTGTGAAAAAGGGTAAAGAACAAAACACACAGCGA
AGCTTTTTTCTCAGAATGAAGTGTACCCTAACTAGCCGAGGAAGAACTATGAACATAAA
GTCTGCAACATGGAAGGTATTGCACTGCACAGGCCACATTCACGTATATGATACCAACA
GTAACCAACCTCAGTGTGGGTATAAGAAACCACCTATGACCTGCTTGGTGCTGATTTGT
GAACCCATTCCTCACCCATCAAATATTGAAATTCCTTTAGATAGCAAGACTTTCCTCAG
TCGACACAGCCTGGATATGAAATTTTCTTATTGTGATGAAAGAATTACCGAATTGATGG
GATATGAGCCAGAAGAACTTTTAGGCCGCTCAATTTATGAATATTATCATGCTTTGGAC
TCTGATCATCTGACCAAAACTCATCATGATATGTTTACTAAAGGACAAGTCACCACAGG
ACAGTACAGGATGCTTGCCAAAAGAGGTGGATATGTCTGGGTTGAAACTCAAGCAACTG
TCATATATAACACCAAGAATTCTCAACCACAGTGCATTGTATGTGTGAATTACGTTGTG
AGTGGTATTATTCAGCACGACTTGATTTCTCCCTTCAACAAACAGAATGTGTCCTTAA
ACCGGTTGAATCTTCAGATATGAAAATGACTCAGCTATTCACCAAAGTTGAATCAGAAG
ATACAAGTAGCCTCTTTGACAAACTTAAGAAGGAACCTGATGCTTTAACTTTGCTGGCC
CCAGCCGCTGGAGACACAATCATATCTTTAGATTTTGGCAGCAACGACACAGAAACTGA
TGACCAGCAACTTGAGGAAGTACCATTATATAATGATGTAATGCTCCCCTCACCCAACG
AAAAATTACAGAATATAAATTTGGCAATGTCTCCATTACCCACCGCTGAAACGCCAAAG
CCACTTCGAAGTAGTGCTGACCCTGCACTCAATCAAGAAGTTGCATTAAAATTAGAACC
AAATCCAGAGTCACTGGAACTTTCTTTTACCATGCCCCAGATTCAGGATCAGACACCTA
GTCCTTCCGATGGAAGCACTAGACAAAGTTCACCTGAGCCTAATAGTCCCAGTGAATAT
TGTTTTTATGTGGATAGTGATATGGTCAATGAATTCAAGTTGGAATTGGTAGAAAAACT
TTTTGCTGAAGACACAGAAGCAAAGAACCCATTTTCTACTCAGGACACAGATTTAGACT
TGGAGATGTTAGCTCCCTATATCCCAATGGATGATGACTTCCAGTTACGTTCCTTCGAT
CAGTTGTCACCATTAGAAAGCAGTTCCGCAAGCCCTGAAAGCGCAAGTCCTCAAAGCAC
AGTTACAGTATTCCAGCAGACTCAAATACAAGAACCTACTGCTAATGCCACCACTACCA
CTGCCACCACTGATGAATTAAAAACAGTGACAAAAGACCGTATGGAAGACATTAAAATA
TTGATTGCATCTCCATCTCCTACCCACATACATAAAGAAACTACTAGTGCCACATCATC
ACCATATAGAGATACTCAAAGTCGGACAGCCTCACCAAACAGAGCAGGAAAAGGAGTCA
TAGAACAGACAGAAAATCTCATCCAAGAAGCCCTAACGTGTTATCTGTCGCTTTGAGT
CAAAGAACTACAGTTCCTGAGGAAGAACTAAATCCAAAGATACTAGCTTTGCAGAATGC
TCAGAGAAAGCGAAAAATGGAACATGATGGTTCACTTTTTCAAGCAGTAGGAATTGGAA
CATTATTACAGCAGCCAGACGATCATGCAGCTACTACATCACTTTCTTGGAAACGTGTA
AAAGGATGCAAATCTAGTGAACAGAATGGAATGGAGCAAAAGACAATTATTTAATACC
CTCTGATTTAGCATGTAGACTGCTGGGGCAATCAATGGATGAAAGTGGATTACCACAGC
TGACCAGTTATGATTGTGAAGTTAATGCTCCTATACAAGGCAGCAGAAACCTACTGCAG
GGTGAAGAATTACTCAGAGCTTTGGATCAAGTTAAC
```

FIG. 9

MetGluGlyAlaGlyGlyAlaAsnAspLysLysLysIleSerSerGluArgArgLysGlu
LysSerArgAspAlaAlaArgSerArgArgSerLysGluSerGluValPheTyrGluLeu
AlaHisGlnLeuProLeuProHisAsnValSerSerHisLeuAspLysAlaSerValMet
ArgLeuThrIleSerTyrLeuArgValArgLysLeuLeuAspAlaGlyAspLeuAspIle
GluAspAspMetLysAlaGlnMetAsnCysPheTyrLeuLysAlaLeuAspGlyPheVal
MetValLeuThrAspAspGlyAspMetIleTyrIleSerAspAsnValAsnLysTyrMet
GlyLeuThrGlnPheGluLeuThrGlyHisSerValPheAspPheThrHisProCysAsp
HisGluGluMetArgGluMetLeuThrHisArgAsnGlyLeuValLysLysGlyLysGlu
GlnAsnThrGlnArgSerPhePheLeuArgMetLysCysThrLeuThrSerArgGlyArg
ThrMetAsnIleLysSerAlaThrTrpLysValLeuHisCysThrGlyHisIleHisVal
TyrAspThrAsnSerAsnGlnProGlnCysGlyTyrLysLysProProMetThrCysLeu
ValLeuIleCysGluProIleProHisProSerAsnIleGluIleProLeuAspSerLys
ThrPheLeuSerArgHisSerLeuAspMetLysPheSerTyrCysAspGluArgIleThr
GluLeuMetGlyTyrGluProGluGluLeuLeuGlyArgSerIleTyrGluTyrTyrHis
AlaLeuAspSerAspHisLeuThrLysThrHisHisAspMetPheThrLysGlyGlnVal
ThrThrGlyGlnTyrArgMetLeuAlaLysArgGlyGlyTyrValTrpValGluThrGln
AlaThrValIleTyrAsnThrLysAsnSerGlnProGlnCysIleValCysValAsnTyr
ValValSerGlyIleIleGlnHisAspLeuIlePheSerLeuGlnGlnThrGluCysVal
LeuLysProValGluSerSerAspMetLysMetThrGlnLeuPheThrLysValGluSer
GluAspThrSerSerLeuPheAspLysLeuLysLysGluProAspAlaLeuThrLeuLeu
AlaProAlaAlaGlyAspThrIleIleSerLeuAspPheGlySerAsnAspThrGluThr
AspAspGlnGlnLeuGluGluValProLeuTyrAsnAspValMetLeuProSerProAsn
GluLysLeuGlnAsnIleAsnLeuAlaMetSerProLeuProThrAlaGluThrProLys
ProLeuArgSerSerAlaAspProAlaLeuAsnGlnGluValAlaLeuLysLeuGluPro
AsnProGluSerLeuGluLeuSerPheThrMetProGlnIleGlnAspGlnThrProSer
ProSerAspGlySerThrArgGlnSerSerProGluProAsnSerProSerGluTyrCys
PheTyrValAspSerAspMetValAsnGluPheLysLeuGluLeuValGluLysLeuPhe
AlaGluAspThrGluAlaLysAsnProPheSerThrGlnAspThrAspLeuAspLeuGlu
MetLeuAlaProTyrIleProMetAspAspAspPheGlnLeuArgSerPheAspGlnLeu
SerProLeuGluSerSerSerAlaSerProGluSerAlaSerProGlnSerThrValThr
ValPheGlnGlnThrGlnIleGlnGluProThrAlaAsnAlaThrThrThrThrAlaThr
ThrAspGluLeuLysThrValThrLysAspArgMetGluAspIleLysIleLeuIleAla
SerProSerProThrHisIleHisLysGluThrThrSerAlaThrSerSerProTyrArg
AspThrGlnSerArgThrAlaSerProAsnArgAlaGlyLysGlyValIleGluGlnThr
GluLysSerHisProArgSerProAsnValLeuSerValAlaLeuSerGlnArgThrThr
ValProGluGluGluLeuAsnProLysIleLeuAlaLeuGlnAsnAlaGlnArgLysArg
LysMetGluHisAspGlySerLeuPheGlnAlaValGlyIleGlyThrLeuLeuGlnGln
ProAspAspHisAlaAlaThrThrSerLeuSerTrpLysArgValLysGlyCysLysSer
SerGluGlnAsnGlyMetGluGlnLysThrIleIleLeuIleProSerAspLeuAlaCys
ArgLeuLeuGlyGlnSerMetAspGluSerGlyLeuProGlnLeuThrSerTyrAspCys
GluValAsnAlaProIleGlnGlySerArgAsnLeuLeuGlnGlyGluGluLeuLeuArg
AlaLeuAspGlnValAsn

FIG. 10

SEQUENCE LISTING

<160> NUMBER OF SEQ ID NOS: 4

<210> SEQ ID NO 1
<211> LENGTH: 1869
<212> TYPE: DNA
<213> ORGANISM: HUMAN

<400> SEQUENCE: 1

```
atggagggcg ccggcggcgc gaacgacaag aaaaagataa gttctgaacg tcgaaaagaa      60
aagtctcgag atgcagccag atctcggcga agtaaagaat ctgaagtttt ttatgagctt     120
gctcatcagt tgccacttcc acataatgtg agttcgcatc ttgataaggc ctctgtgatg     180
aggcttacca tcagctattt gcgtgtgagg aaacttctgg atgctggtga tttggatatt     240
gaagatgaca tgaaagcaca gatgaattgc ttttatttga aagccttgga tggttttgtt     300
atggttctca cagatgatgg tgacatgatt tacatttctg ataatgtgaa caaatacatg     360
ggattaactc agtttgaact aactggacac agtgtgtttg attttactca tccatgtgac     420
catgaggaaa tgagagaaat gcttacacac agaaatggcc ttgtgaaaaa gggtaaagaa     480
caaaacacac agcgaagctt ttttctcaga atgaagtgta ccctaactag ccgaggaaga     540
actatgaaca taaagtctgc aacatggaag gtattgcact gcacaggcca cattcacgta     600
tatgatacca acagtaacca acctcagtgt gggtataaga aaccacctat gacctgcttg     660
gtgctgattt gtgaacccat tcctcaccca tcaaatattg aaattccttt agatagcaag     720
actttcctca gtcgacacag cctggatatg aaattttctt attgtgatga aagaattacc     780
gaattgatgg gatatgagcc agaagaactt ttaggccgct caatttatga atattatcat     840
gctttggact ctgatcatct gaccaaaact catcatgata tgtttactaa aggacaagtc     900
accacaggac agtacaggat gcttgccaaa agaggtggat atgtctgggt tgaaactcaa     960
```

```
gcaactgtca tatataacac caagaattct caaccacagt gcattgtatg tgtgaattac    1020
gttgtgagtg gtattattca gcacgacttg attttctccc ttcaacaaac agaatgtgtc    1080
cttaaaccgg ttgaatcttc agatatgaaa atgactcagc tattcaccaa agttgaatca    1140
gaagatacaa gtagcctctt tgacaaactt aagaaggaac ctgatgcttt aactttgctg    1200
cagactcaaa tacaagaacc tactgctaat gccaccacta ccactgccac cactgatgaa    1260
ttaaaaacag tgacaaaaga ccgtatggaa gacattaaaa tattgattgc atctccatct    1320
cctacccaca tacataaaga aactactagt gccacatcat caccatatag agatactcaa    1380
agtcggacag cctcaccaaa cagagcagga aaggagtca tagaacagac agaaaaatct    1440
catccaagaa gccctaacgt ttatctgtc gctttgagtc aaagaactac agttcctgag    1500
gaagaactaa atccaaagat actagctttg cagaatgctc agagaaagcg aaaaatggaa    1560
catgatggtt cacttttca gcagtagga attggaacat tattcagca gccagacgat    1620 catgcagcta ctacatcact ttcttggaaa cgtgtaaaag gatgcaaatc tagtgaacag    1680
aatggaatgg agcaaaagac aattatttta ataccctctg atttagcatg tagactgctg    1740
gggcaatcaa tggatgaaag tggattacca cagctgacca gttatgattg tgaagttaat    1800
gctcctatac aaggcagcag aaacctactg cagggtgaag aattactcag agctttggat    1860
caagttaac                                                           1869

<210> SEQ ID NO 2
<211> LENGTH: 623
<212> TYPE: PRT
<213> ORGANISM: HUMAN

<400> SEQUENCE: 2
```

Met Glu Gly Ala Gly Gly Ala Asn Asp Lys Lys Ile Ser Ser Glu
 1               5                  10                  15

Arg Arg Lys Glu Lys Ser Arg Asp Ala Ala Arg Ser Arg Ser Lys
                20                  25                  30

Glu Ser Glu Val Phe Tyr Glu Leu Ala His Gln Leu Pro Leu Pro His
                35                  40                  45

Asn Val Ser Ser His Leu Asp Lys Ala Ser Val Met Arg Leu Thr Ile
        50                  55                  60

Ser Tyr Leu Arg Val Arg Lys Leu Leu Asp Ala Gly Asp Leu Asp Ile
65                  70                  75                  80

Glu Asp Asp Met Lys Ala Gln Met Asn Cys Phe Tyr Leu Lys Ala Leu
                85                  90                  95

Asp Gly Phe Val Met Val Leu Thr Asp Asp Gly Asp Met Ile Tyr Ile
                100                 105                 110

Ser Asp Asn Val Asn Lys Tyr Met Gly Leu Thr Gln Phe Glu Leu Thr
        115                 120                 125

Gly His Ser Val Phe Asp Phe Thr His Pro Cys Asp His Glu Glu Met
    130                 135                 140

Arg Glu Met Leu Thr His Arg Asn Gly Leu Val Lys Lys Gly Lys Glu
145                 150                 155                 160

Gln Asn Thr Gln Arg Ser Phe Phe Leu Arg Met Lys Cys Thr Leu Thr
                165                 170                 175

Ser Arg Gly Arg Thr Met Asn Ile Lys Ser Ala Thr Trp Lys Val Leu
                180                 185                 190

His Cys Thr Gly His Ile His Val Tyr Asp Thr Asn Ser Asn Gln Pro
        195                 200                 205

-continued

```
Gln Cys Gly Tyr Lys Lys Pro Met Thr Cys Leu Val Leu Ile Cys
    210                 215                 220
Glu Pro Ile Pro His Pro Ser Asn Ile Glu Ile Pro Leu Asp Ser Lys
225                 230                 235                 240
Thr Phe Leu Ser Arg His Ser Leu Asp Met Lys Phe Ser Tyr Cys Asp
                245                 250                 255
Glu Arg Ile Thr Glu Leu Met Gly Tyr Glu Pro Glu Glu Leu Leu Gly
            260                 265                 270
Arg Ser Ile Tyr Glu Tyr Tyr His Ala Leu Asp Ser Asp His Leu Thr
        275                 280                 285
Lys Thr His His Asp Met Phe Thr Lys Gly Gln Val Thr Thr Gly Gln
    290                 295                 300
Tyr Arg Met Leu Ala Lys Arg Gly Gly Tyr Val Trp Val Glu Thr Gln
305                 310                 315                 320
Ala Thr Val Ile Tyr Asn Thr Lys Asn Ser Gln Pro Gln Cys Ile Val
                325                 330                 335
Cys Val Asn Tyr Val Val Ser Gly Ile Ile Gln His Asp Leu Ile Phe
            340                 345                 350
Ser Leu Gln Gln Thr Glu Cys Val Leu Lys Pro Val Glu Ser Ser Asp
        355                 360                 365
Met Lys Met Thr Gln Leu Phe Thr Lys Val Glu Ser Glu Asp Thr Ser
    370                 375                 380
Ser Leu Phe Asp Lys Leu Lys Lys Glu Pro Asp Ala Leu Thr Leu Leu
385                 390                 395                 400
Gln Thr Gln Ile Gln Glu Pro Thr Ala Asn Ala Thr Thr Thr Thr Ala
                405                 410                 415
Thr Thr Asp Glu Leu Lys Thr Val Thr Lys Asp Arg Met Glu Asp Ile
            420                 425                 430
Lys Ile Leu Ile Ala Ser Pro Ser Pro Thr His Ile His Lys Glu Thr
        435                 440                 445
Thr Ser Ala Thr Ser Ser Pro Tyr Arg Asp Thr Gln Ser Arg Thr Ala
    450                 455                 460
Ser Pro Asn Arg Ala Gly Lys Gly Val Ile Glu Gln Thr Glu Lys Ser
465                 470                 475                 480
His Pro Arg Ser Pro Asn Val Leu Ser Val Ala Leu Ser Gln Arg Thr
                485                 490                 495
Thr Val Pro Glu Glu Glu Leu Asn Pro Lys Ile Leu Ala Leu Gln Asn
            500                 505                 510
Ala Gln Arg Lys Arg Lys Met Glu His Asp Gly Ser Leu Phe Gln Ala
        515                 520                 525
Val Gly Ile Gly Thr Leu Leu Gln Gln Pro Asp Asp His Ala Ala Thr
    530                 535                 540
Thr Ser Leu Ser Trp Lys Arg Val Lys Gly Cys Lys Ser Ser Glu Gln
545                 550                 555                 560
Asn Gly Met Glu Gln Lys Thr Ile Ile Leu Ile Pro Ser Asp Leu Ala
                565                 570                 575
Cys Arg Leu Leu Gly Gln Ser Met Asp Glu Ser Gly Leu Pro Gln Leu
            580                 585                 590
Thr Ser Tyr Asp Cys Glu Val Asn Ala Pro Ile Gln Gly Ser Arg Asn
        595                 600                 605
Leu Leu Gln Gly Glu Glu Leu Leu Arg Ala Leu Asp Gln Val Asn
    610                 615                 620
```

<210> SEQ ID NO 3
<211> LENGTH: 2517
<212> TYPE: DNA
<213> ORGANISM: HUMAN

<400> SEQUENCE: 3

| | | | | | |
|---|---|---|---|---|---|
| gtgaagacat | cgcggggacc | gattcaccat | ggagggcgcc | ggcggcgcga | agacaagaac | 60 |
| gacaagaaaa | agataagttc | tgaacgtcga | aagaaaagt | ctcgagatgc | agccagatct | 120 |
| cggcgaagta | agaatctga | agtttttat | gagcttgctc | atcagttgcc | acttccacat | 180 |
| aatgtgagtt | cgcatcttga | taaggcctct | gtgatgaggc | ttaccatcag | ctatttgcgt | 240 |
| gtgaggaaac | ttctggatgc | tggtgatttg | atattgaag | atgacatgaa | agcacagatg | 300 |
| aattgctttt | atttgaaagc | cttggatggt | tttgttatgg | ttctcacaga | tgatggtgac | 360 |
| atgatttaca | tttctgataa | tgtgaacaaa | tacatgggat | taactcagtt | tgaactaact | 420 |
| ggacacagtg | tgtttgattt | tactcatcca | tgtgaccatg | aggaaatgag | agaaatgctt | 480 |
| acacacagaa | atggccttgt | gaaaagggt | aaagaacaaa | acacacagcg | aagcttttt | 540 |
| ctcagaatga | agtgtaccct | aactagccga | ggaagaacta | tgaacataaa | gtctgcaaca | 600 |
| tggaaggtat | tgcactgcac | aggccacatt | cacgtatatg | ataccaacag | taaccaacct | 660 |
| cagtgtgggt | ataagaaacc | acctatgacc | tgcttggtgc | tgatttgtga | acccattcct | 720 |
| cacccatcaa | atattgaaat | tcctttagat | agcaagactt | tcctcagtcg | cacacagcctg | 780 |
| gatatgaaat | tttcttattg | tgatgaaaga | attaccgaat | tgatgggata | tgagccagaa | 840 |
| gaacttttag | gccgctcaat | ttatgaatat | tatcatgctt | tggactctga | tcatctgacc | 900 |
| aaaactcatc | atgatatgtt | tactaaagga | caagtcacca | caggacagta | caggatgctt | 960 |
| gccaaaagag | gtggatatgt | ctgggttgaa | actcaagcaa | ctgtcatata | taacaccaag | 1020 |
| aattctcaac | cacagtgcat | tgtatgtgtg | aattacgttg | tgagtggtat | tattcagcac | 1080 |
| gacttgattt | tctcccttca | acaaacagaa | tgtgtcctta | accggttga | atcttcagat | 1140 |
| atgaaaatga | ctcagctatt | caccaaagtt | gaatcagaag | atacaagtag | cctctttgac | 1200 |
| aaacttaaga | aggaacctga | tgctttaact | ttgctggccc | cagccgctgg | agacacaatc | 1260 |
| atatctttag | attttggcag | caacgacaca | gaaactgatg | accagcaact | tgaggaagta | 1320 |
| ccattatata | atgatgtaat | gctcccctca | cccaacgaaa | aattacagaa | tataaatttg | 1380 |
| gcaatgtctc | cattcccac | cgctgaaacg | ccaaagccac | ttcgaagtag | tgctgaccct | 1440 |
| gcactcaatc | aagaagttgc | attaaaatta | gaaccaaatc | cagagtcact | ggaactttct | 1500 |
| tttaccatgc | cccagattca | ggatcagaca | cctagtcctt | ccgatggaag | cactagacaa | 1560 |
| agttcacctg | agcctaatag | tcccagtgaa | tattgttttt | atgtggatag | tgatatggtc | 1620 |
| aatgaattca | agttggaatt | ggtagaaaaa | cttttgctg | aagacacaga | agcaaagaac | 1680 |
| ccattttcta | ctcaggacac | agatttagac | ttggagatgt | tagctcccta | tatcccaatg | 1740 |
| gatgatgact | ccagttacg | ttccttcgat | cagttgtcac | cattagaaag | cagttccgca | 1800 |
| agccctgaaa | gcgcaagtcc | tcaaagcaca | gttacagtat | tccagcagac | tcaaatacaa | 1860 |
| gaacctactg | ctaatgccac | cactaccact | gccaccactg | atgaattaaa | aacagtgaca | 1920 |
| aaagaccgta | tggaagacat | taaaatattg | attgcatctc | catctcctac | ccacatacat | 1980 |
| aaagaaacta | ctagtgccac | atcatcacca | tatagagata | tcaaagtcg | acagcctca | 2040 |
| ccaaacagag | caggaaaagg | agtcatgaa | cagacagaaa | aatctcatcc | aagaagccct | 2100 |
| aacgtgttat | ctgtcgcttt | gagtcaaaga | actacagttc | ctgaggaaga | actaaatcca | 2160 |

-continued

```
aagatactag ctttgcagaa tgctcagaga aagcgaaaaa tggaacatga tggttcactt    2220
tttcaagcag taggaattgg aacattatta cagcagccag acgatcatgc agctactaca    2280
tcactttctt ggaaacgtgt aaaaggatgc aaatctagtg aacagaatgg aatggagcaa    2340
aagacaatta ttttaatacc ctctgattta gcatgtagac tgctggggca atcaatggat    2400
gaaagtggat taccacagct gaccagttat gattgtgaag ttaatgctcc tatacaaggc    2460
agcagaaacc tactgcaggg tgaagaatta ctcagagctt tggatcaagt taactga      2517
```

<210> SEQ ID NO 4
<211> LENGTH: 826
<212> TYPE: PRT
<213> ORGANISM: HUMAN

<400> SEQUENCE: 4

| Met | Glu | Gly | Ala | Gly | Gly | Ala | Asn | Asp | Lys | Lys | Ile | Ser | Ser | Glu |
|---|---|---|---|---|---|---|---|---|---|---|---|---|---|---|
| 1 | | | | 5 | | | | | 10 | | | | | 15 |

| Arg | Arg | Lys | Glu | Lys | Ser | Arg | Asp | Ala | Ala | Arg | Ser | Arg | Arg | Ser | Lys |
|---|---|---|---|---|---|---|---|---|---|---|---|---|---|---|---|
| | | | 20 | | | | | 25 | | | | | 30 | | |

Glu Ser Glu Val Phe Tyr Glu Leu Ala His Gln Leu Pro Leu Pro His
            35                  40                  45

Asn Val Ser Ser His Leu Asp Lys Ala Ser Val Met Arg Leu Thr Ile
        50                  55                  60

Ser Tyr Leu Arg Val Arg Lys Leu Leu Asp Ala Gly Asp Leu Asp Ile
65                  70                  75                  80

Glu Asp Asp Met Lys Ala Gln Met Asn Cys Phe Tyr Leu Lys Ala Leu
                85                  90                  95

Asp Gly Phe Val Met Val Leu Thr Asp Asp Gly Asp Met Ile Tyr Ile
            100                 105                 110

Ser Asp Asn Val Asn Lys Tyr Met Gly Leu Thr Gln Phe Glu Leu Thr
        115                 120                 125

Gly His Ser Val Phe Asp Phe Thr His Pro Cys Asp His Glu Glu Met
    130                 135                 140

Arg Glu Met Leu Thr His Arg Asn Gly Leu Val Lys Lys Gly Lys Glu
145                 150                 155                 160

Gln Asn Thr Gln Arg Ser Phe Phe Leu Arg Met Lys Cys Thr Leu Thr
                165                 170                 175

Ser Arg Gly Arg Thr Met Asn Ile Lys Ser Ala Thr Trp Lys Val Leu
            180                 185                 190

His Cys Thr Gly His Ile His Val Tyr Asp Thr Asn Ser Asn Gln Pro
        195                 200                 205

Gln Cys Gly Tyr Lys Lys Pro Pro Met Thr Cys Leu Val Leu Ile Cys
    210                 215                 220

Glu Pro Ile Pro His Pro Ser Asn Ile Glu Ile Pro Leu Asp Ser Lys
225                 230                 235                 240

Thr Phe Leu Ser Arg His Ser Leu Asp Met Lys Phe Ser Tyr Cys Asp
                245                 250                 255

Glu Arg Ile Thr Glu Leu Met Gly Tyr Glu Pro Glu Glu Leu Leu Gly
            260                 265                 270

Arg Ser Ile Tyr Glu Tyr Tyr His Ala Leu Asp Ser Asp His Leu Thr
        275                 280                 285

Lys Thr His His Asp Met Phe Thr Lys Gly Gln Val Thr Thr Gly Gln
    290                 295                 300

Tyr Arg Met Leu Ala Lys Arg Gly Gly Tyr Val Trp Val Glu Thr Gln

-continued

```
            305                 310                 315                 320
        Ala Thr Val Ile Tyr Asn Thr Lys Asn Ser Gln Pro Gln Cys Ile Val
                        325                 330                 335
        Cys Val Asn Tyr Val Val Ser Gly Ile Ile Gln His Asp Leu Ile Phe
                        340                 345                 350
        Ser Leu Gln Gln Thr Glu Cys Val Leu Lys Pro Val Glu Ser Ser Asp
                        355                 360                 365
        Met Lys Met Thr Gln Leu Phe Thr Lys Val Glu Ser Glu Asp Thr Ser
                        370                 375                 380
        Ser Leu Phe Asp Lys Leu Lys Lys Glu Pro Asp Ala Leu Thr Leu Leu
        385                 390                 395                 400
        Ala Pro Ala Ala Gly Asp Thr Ile Ile Ser Leu Asp Phe Gly Ser Asn
                        405                 410                 415
        Asp Thr Glu Thr Asp Asp Gln Gln Leu Glu Glu Val Pro Leu Tyr Asn
                        420                 425                 430
        Asp Val Met Leu Pro Ser Pro Asn Glu Lys Leu Gln Asn Ile Asn Leu
                        435                 440                 445
        Ala Met Ser Pro Leu Pro Thr Ala Glu Thr Pro Lys Pro Leu Arg Ser
                        450                 455                 460
        Ser Ala Asp Pro Ala Leu Asn Gln Glu Val Ala Leu Lys Leu Glu Pro
        465                 470                 475                 480
        Asn Pro Glu Ser Leu Glu Leu Ser Phe Thr Met Pro Gln Ile Gln Asp
                        485                 490                 495
        Gln Thr Pro Ser Pro Ser Asp Gly Ser Thr Arg Gln Ser Ser Pro Glu
                        500                 505                 510
        Pro Asn Ser Pro Ser Glu Tyr Cys Phe Tyr Val Asp Ser Asp Met Val
                        515                 520                 525
        Asn Glu Phe Lys Leu Glu Leu Val Glu Lys Leu Phe Ala Glu Asp Thr
                        530                 535                 540
        Glu Ala Lys Asn Pro Phe Ser Thr Gln Asp Thr Asp Leu Asp Leu Glu
        545                 550                 555                 560
        Met Leu Ala Pro Tyr Ile Pro Met Asp Asp Asp Phe Gln Leu Arg Ser
                        565                 570                 575
        Phe Asp Gln Leu Ser Pro Leu Glu Ser Ser Ser Ala Ser Pro Glu Ser
                        580                 585                 590
        Ala Ser Pro Gln Ser Thr Val Thr Val Phe Gln Gln Thr Gln Ile Gln
                        595                 600                 605
        Glu Pro Thr Ala Asn Ala Thr Thr Thr Thr Ala Thr Thr Asp Glu Leu
                        610                 615                 620
        Lys Thr Val Thr Lys Asp Arg Met Glu Asp Ile Lys Ile Leu Ile Ala
        625                 630                 635                 640
        Ser Pro Ser Pro Thr His Ile His Lys Glu Thr Thr Ser Ala Thr Ser
                        645                 650                 655
        Ser Pro Tyr Arg Asp Thr Gln Ser Arg Thr Ala Ser Pro Asn Arg Ala
                        660                 665                 670
        Gly Lys Gly Val Ile Glu Gln Thr Glu Lys Ser His Pro Arg Ser Pro
                        675                 680                 685
        Asn Val Leu Ser Val Ala Leu Ser Gln Arg Thr Thr Val Pro Glu Glu
                        690                 695                 700
        Glu Leu Asn Pro Lys Ile Leu Ala Leu Gln Asn Ala Gln Arg Lys Arg
        705                 710                 715                 720
        Lys Met Glu His Asp Gly Ser Leu Phe Gln Ala Val Gly Ile Gly Thr
                        725                 730                 735
```

```
Leu Leu Gln Gln Pro Asp Asp His Ala Ala Thr Thr Ser Leu Ser Trp
        740             745                 750

Lys Arg Val Lys Gly Cys Lys Ser Ser Glu Gln Asn Gly Met Glu Gln
        755             760                 765

Lys Thr Ile Ile Leu Ile Pro Ser Asp Leu Ala Cys Arg Leu Leu Gly
        770             775             780

Gln Ser Met Asp Glu Ser Gly Leu Pro Gln Leu Thr Ser Tyr Asp Cys
785             790             795                 800

Glu Val Asn Ala Pro Ile Gln Gly Ser Arg Asn Leu Leu Gln Gly Glu
            805             810                 815

Glu Leu Leu Arg Ala Leu Asp Gln Val Asn
            820             825
```

USE OF HIF-1A VARIANTS TO ACCELERATE WOUND HEALING

GOVERNMENT SUPPORT

This invention was made with Government support under Grant No. R01-CA71398, awarded by the National Institutes of Health. The Government has certain rights in this invention.

BACKGROUND OF THE INVENTION

1. Field of the Invention

The present invention relates to the use of stable HIF-1α variants in accelerating wound healing.

2. Description of the Related Art

HIF-1

Hypoxia-inducible factor-1 (HIF-1) is a mammalian transcription factor that is expressed in response to hypoxia (Wang et al. 1995. Proc. Natl. Acad. Sci. USA 92: 5510–5514). HIF-1 transactivates genes encoding several glucose transporters and glycolytic enzymes, as well as genes increasing tissue perfusion such as vascular endothelial growth factor (VEGF), inducible nitric oxide synthase, and erythropoietin (Semenza, G. 1999. *Annual Review Cell and Development Biology* 15: 551–78.). HIF-1 is a heterodimeric molecule composed of a labile alpha (HIF-1α) and a constitutive beta (HIF-1β/ARNT aryl hydrocarbon nuclear transporter) subunit. In normoxia (normal oxygen tension), HIF-1α protein is rapidly degraded via ubiquitination and proteasomal digestion. In contrast HIF-1β is stable and equivalently expressed in normoxia and hypoxia. Thus the major regulation of the transcriptional activity of HIF-1 is due to the HIF-1α component.

Structural analysis of HIF-1α has indicated that dimerization requires two domains that have been termed HLH and PAS, while DNA binding is mediated by a basic domain (Semenza et al. 1997. Kid. Int. 51: 553–555). Further, two transactivation domains have been identified in the C-terminal half of HIF-1α (Jiang, et al. 1997. J. Biol. Chem. 272: 19253–19260).

HIF-1α degradation is mediated by an approximately 200-amino acid domain that has been termed the "oxygen-dependent degradation domain" (ODD) (Huang, L., J. Gu, M. Schau, and H. Bunn. 1998. Proc. Natl. Acad. Sci. U.S.A. 95: 7987–92). Cells transfected with cDNA encoding HIF-1α in which the ODD is deleted (HIF-1αΔODD) demonstrate constitutively active HIF-1α protein regardless of oxygen tension (Huang, L., J. Gu, M. Schau, and H. Bunn. 1998. Proc. Natl. Acad. Sci. U.S.A. 95: 7987–92). A number of stable forms of HIF-1α with deletions in the ODD are described in U.S. Pat. No. 6,124,131.

HIF-1α is required for both embryonic development (Ryan, H., J. Lo, and R. Johnson. 1998. EMBO Journal 17: 3005–15) (Iyer, N. et al. 1998. Genes and Development 12: 149–62) and growth of tumor explants (Ryan, H., J. Lo, and R. Johnson. 1998. EMBO Journal 17: 3005–15), which underscores a central role of this molecule in the hypoxic response in vivo. In adult animals HIF-1α is overexpressed in epithelial cancers and high-grade pre-malignant lesions (Zhong, H., et al. 1998. Cancer Research 58: 5280–5284), ischemic cardiac muscle (Lee, S., et al. 2000b. New England Journal of Medicine 342: 626–633), and healing wounds (Elson, D. et al. 2000. Cancer Research 60: 6189–6195).

Wound Healing

Wound healing is a multistep, multicellular process that involves shifting oxygen levels in the wound environment. The initial step of wound healing is characterized by clotting, fibrin formation, and neutrophil infiltration. Neutrophil infiltration provides phagocytic and lysosomal activity. A second step involves macrophage and fibroblast infiltration into the wound thereby facilitating debridement and inflammation. In this second step, enzymes are secreted which digest cellular debris and breakdown intercellular matrices which anchor such cellular debris. Thus, through both phagocytosis and the activity of secreted enzymes, large scale removal of wound debris is effected. Anoxic conditions prevail in the interior of the wound until the completion of angiogenesis; i.e., approximately one week after wounding. Subsequent steps involve fibroblast proliferation; extensive collagen production; capillary formation; and finally myofibroblast contraction leading to compression, disappearance of capillaries, and scar tissue formation.

The process of wound healing begins immediately after formation of a wound and involves numerous cell types and complex interactions between multiple biochemical cascades. Growth factors released in the traumatized area stimulate and promote wound healing, such as by stimulating cell migration into the wound area (chemotaxis), proliferation of epithelial cells, muscle cells, endothelial cells, blood cells and fibroblasts (mitogenesis), formation of new blood vessels (angiogenesis), and matrix formation and remodeling of the affected region including re-epithelization by keratinocytes.

Factors that stimulate or accelerate wound healing will find a variety of uses but are of particular importance in the treatment of patients with chronic wounds which may require daily treatment, represent a constant source of pain to the patient, may lead to life threatening infection and are a significant medical expense. Chronic wounds are those which are slow-healing or which do not heal at all and are common to diabetics, cancer patients and those confined to bed for long periods of time.

SUMMARY OF THE INVENTION

In one aspect the present invention provides a method of accelerating wound healing in a mammal comprising administering to the mammal, preferably a human, a stable variant of an HIF-1α polypeptide comprising an oxygen-dependent degradation domain (ODD). The stable HIF-1α variant preferably comprises an insertion, substitution or deletion within the oxygen-dependent degradation domain (ODD). In one embodiment the stable HIF-1α variant comprises a deletion of the ODD. The preferred variant comprises the amino acid sequence of SEQ ID NO: 2.

In one embodiment the stable HIF-1α variant polypeptide is administered topically. It may be administered directly to the wound.

In one embodiment the wound is caused by mechanical, chemical or thermal means. The wound may be a contusion, incision or laceration. In a further embodiment the wound is the result of a surgical incision.

In another embodiment the wound is associated with a disease or disorder, such as diabetes. In particular, the wound may be a diabetic ulcer.

Another compound useful in the treatment of the wound may be administered with the stable HIF-1α variant, such as a growth factor. In one embodiment VEGF is administered with the variant.

In another aspect the invention provides a method of accelerating wound healing in a mammal comprising transfecting cells in or near the wound with nucleic acid encoding a stable variant of an HIF-1α polypeptide, according to claim 1, such that the cells express the stable variant polypeptide.

In a further aspect the invention provides a pharmaceutical composition comprising a stable HIF-1α variant polypeptide according to claim 1 in association with a pharmaceutically acceptable carrier. In one embodiment the pharmaceutical composition is suitable for topical delivery, such as an ointment, cream or gel. In another embodiment the pharmaceutical composition is suitable for systemic delivery.

BRIEF DESCRIPTION OF THE DRAWINGS

FIG. 6 shows the human HIF1αΔODD nucleotide sequence (SEQ ID NO: 1).

FIG. 7 shows the human HIF1αΔODD amino acid sequence (SEQ ID NO: 2).

FIG. 9 shows the nucleotide sequence of human HIF-1α (SEQ ID NO: 3).

FIG. 10 shows the amino acid sequence of human HIF-1α (SEQ ID NO: 4).

DETAILED DESCRIPTION OF THE PREFERRED EMBODIMENT

Figure 1:
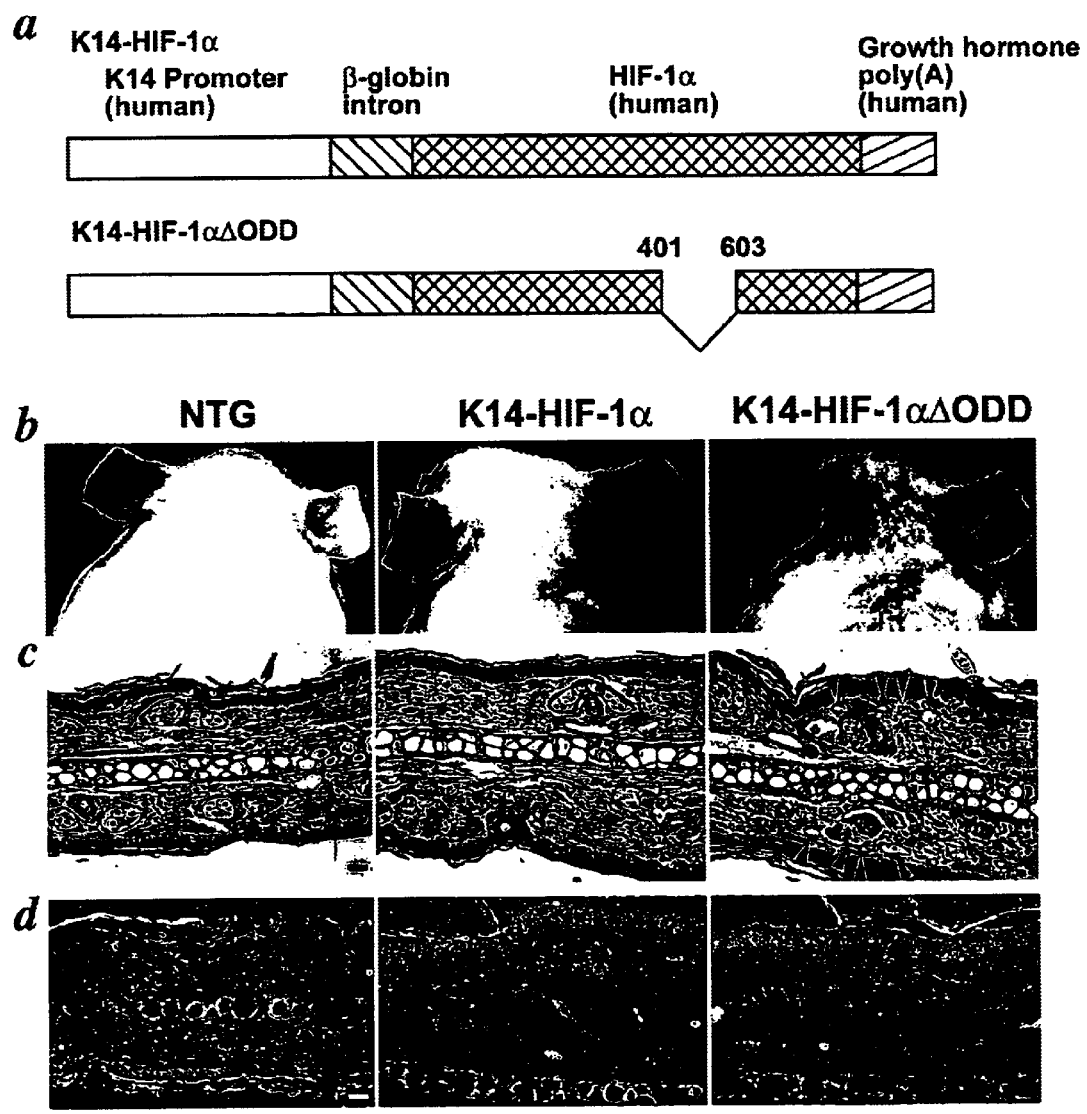
FIGS. 1a–1d. Generation and initial characterization of HIF-1α transgenic mice. (a) Constructs used to target wild type human HIF-1α or mutant HIF-1αΔODD (deletion of the "oxygen-dependent degradation domain" (Huang, L., J. Gu, M. Schau, and H. Bunn. 1998. Proc. Natl. Acad. Sci. U.S.A. 95: 7987–92) to basal keratinocytes (Munz, B. et al. 1999. EMBO Journal 18: 5205–5215). Amino acids spanning the ODD are indicated. (b) Redness and prominent vasculature of ear skin and roughness of coat are evident in the K14-HIF-1αΔODD transgenic mice. K14-HIF-1α transgenic mice are indistinguishable from nontransgenic controls. (c) Histopathology of ears reveals an increase in blood vessels (see green arrowheads) in the dermis of K14-HIF-1αΔODD transgenic mice. No inflammation or edema is detectable. (d) In-situ hybridization with a $^{35}$S labeled riboprobe specific for human HIF-1α. Both HIF-1α and HIF-1αΔODD transgenes are expressed in basal keratinocytes of interfollicular epidermis and the hair follicle outer root sheath, and appear to be expressed at the same level, as visually estimated from silver grain density. Bars (c) and (d), 20 μm.

Unless defined otherwise, technical and scientific terms used herein have the same meaning as commonly understood by one of ordinary skill in the art to which this invention belongs. See, e.g. Singleton et al., *Dictionary of Microbiology and Molecular Biology* 2nd ed., J. Wiley & Sons (New York, N.Y. 1994); Sambrook et al., *Molecular Cloning, A Laboratory Manual*, Cold Springs Harbor Press (Cold Springs Harbor, N.Y. 1989).

As used herein, the terms "HIF-1α" and "HIF-1α polypeptide," which are used interchangeably, refer to native sequence HIF-1α and HIF-1α variants, including mutant forms of HIF-1α. Optionally, the HIF-1α is not associated with native glycosylation. "Native glycosylation" refers to the carbohydrate moieties that are covalently attached to HIF-1α when it is produced in mammalian cells, particularly in the cells in which it is produced in nature. Accordingly, human HIF-1α produced in a non-human cell is an example of HIF-1α that may "not be associated with native glycosylation." Sometimes the HIF-1α may not be glycosylated at all, as in the case where it is produced in prokaryotes, e.g. *E. coli*.

"Native sequence HIF-1α" comprises a polypeptide having the same amino acid sequence as HIF-1α derived from nature, regardless of its mode of preparation. Thus, native sequence HIF-1α can have the amino acid sequence of naturally-occurring human HIF-1α, murine HIF-1α, or HIF-1α from any other mammalian species. For example full-length native sequence human HIF-1α is disclosed in U.S. Pat. No. 5,882,914, which is hereby incorporated by reference. The nucleotide sequence of native human HIF-1α is presented in FIG. 9 (SEQ ID NO: 3) and the amino acid sequence of nnative human HIF-1α is presented in FIG. 10 (SEQ ID NO: 4). Native sequence HIF-1α can be isolated from nature or can be produced by recombinant and/or synthetic means. The term "native sequence HIF-1α" specifically encompasses naturally occurring prepro, pro and mature forms and truncated forms of HIF-1α, naturally-occurring variant forms (e.g. alternatively spliced forms), and naturally-occurring allelic variants.

"HIF-1α variants" and "HIF-1α mutants" are biologically active HIF-1α polypeptides having an amino acid sequence that differs from the sequence of a native sequence HIF-1α polypeptide by virtue of an insertion, deletion, modification and/or substitution of one or more amino acid residues within the native sequence. Thus, HIF-1α variants include HIF-1α polypeptides where a number of amino acid residues are deleted and optionally substituted by one or more amino acid residues. HIF-1α variants also include HIF-1α polypeptides wherein one or more amino acid residues are added at the N- or C-terminus of, or within, a native HIF-1α sequence. HIF-1α variants also may be covalently modified, for example by substitution with a moiety other than a naturally occurring amino acid or by modifying an amino acid residue to produce a non-naturally occurring amino acid.

"Stable HIF-1α," "stable HIF-1α variant" and "stable variant" refer to an HIF-1α variant that is constitutively active regardless of oxygen tension. A stable HIF-1α variant preferably has an increased half-life compared to wild type HIF-1α under non-hypoxic conditions. As discussed below, several stable HIF-1α variants that can be used in the methods disclosed herein are available. Alternatively, HIF-1α variants may be made by well known techniques and stable variants that would be useful in the methods of the present invention identified by their constitutive activity under normoxic conditions using assays known in the art. Stable HIF-1α variants preferably comprise one or more amino acid deletions, insertions or substitutions, particularly in the oxygen dependent degradation domain (ODD). The ODD comprises approximately amino acids 400 to 603 of the native HIF-1α amino acid sequence of FIG. 10 (SEQ ID NO: 4).

Several stable HIF-1α variants that may be used in the methods disclosed herein are provided in U.S. Pat. No. 6,124,131, which is hereby incorporated by reference in its entirety. These include HIF-1α polypeptides wherein amino acids 392 to 428 are deleted, as well as HIF-1α polypeptides wherein amino acids 392 to 520 are deleted. Also disclosed are stable HIF-1α mutants with deletions from amino acid 392 to any amino acid between 429 and 550. It is further taught that any of these deletions can be combined with the mutation of amino acid 551 from a serine to any other amino acid and amino acid 552 from a threonine to any other amino acid.

The preferred stable HIF-1α mutant for use in the present invention comprises a complete deletion of amino acid residues 401 to 603 of the HIF-1α amino acid sequence. The nucleotide sequence of this preferred variant is presented in FIG. 6 (SEQ ID NO: 1) and the amino acid sequence is presented in FIG. 7 (SEQ ID NO: 2). This variant is described in Huang et al. (1998. Proc. Natl. Acad. Sci. U.S.A. 95: 7987–92), which is hereby incorporated by reference.

Stable HIF-1α variants preferably comprise one or more functional HIF-1α transactivation domains. The transactivation domains are located approximately between amino acids 600 and 826 of the native human HIF-1α amino acid sequence of FIG. 10 (SEQ ID NO: 4). More particularly, one transactivation domain comprises approximately amino acids 531 to 575 and a second transactivation domain comprises approximately amino acids 786 to 826. The inclusion of one or more transactivation domains in the stable HIF-1α variant may be advantageous in terms of levels and spectrum of target gene expression compared to a constitutively active mutant with a heterologous transactivation domain (Vincent, K. et al. 2000. Circulation 102: 2255–2261). However, stable HIF-1α variants with a deletion, substitution or insertion in all or part of one or both of the transactivation domains or substitution of one or both of the transactivation domains with a heterologous transactivation domain may also be used. An example of such a variant is HIF-1α/VP16, which comprises the DNA-binding and dimerization domains from HIF-1α with the transactivation domain from herpes simplex virus VP16 protein (Vincent et al. 2000. Circ. 102: 2255–2261, hereby incorporated by reference). This variant has been shown to be a strong, constitutive transcriptional activator and is currently being used in several Phase I clinical trials for the treatment of ischemic heart disease and peripheral vascular disease.

Stable HIF-1α variants have been found to accelerate wound healing, as shown in Example 8 below. It has been shown previously that HIF-1α expression increases during wound healing (Elson et al. 2000. Cancer Res. 60: 89–95). As wounds typically comprise an anoxic environment, stabilization of the wild type HIF-1α would be expected. However, as disclosed in Example 8 below, stabilized HIF-1α variants, particularly HIF-1α with a deleted oxygen dependent degradation domain (ODD), are capable of accelerating wound healing to a greater extent than wild-type HIF-1α.

Thus, in one aspect, the present invention provides methods of accelerating wound healing. Advantageously, the preferred stable HIF-1α variants do not produce side effects such as inflammation and edema when used therapeutically.

In the preferred embodiment, a stable HIF-1α variant is administered to a mammal in an amount effective to accelerate the healing of a wound. In one embodiment the stable HIF-1α variant is administered as a polypeptide. The stable HIF-1α variant polypeptide may be administered systemically. Alternatively it may be administered directly to the site of the wound, such as by topical administration. Administration of stable HIF-1α variant polypeptides is described in more detail below.

The nucleic acid encoding a stable HIF-1α variant may also be used to accelerate wound healing. In one embodiment cells in or near the region of the wound are transfected with nucleic acid encoding the stable HIF-1α variant such that the variant is expressed in those cells and accelerates healing of the wound. The cells may be transfected by any method known in the art. For example, the nucleic acid may be incorporated into a viral vector that is allowed to infect the desired cells. Such viral vectors are well known in the art. Several exemplary viral vectors that can be utilized for gene therapy include adenovirus, adeno-associated virus, herpes virus, vaccinia virus, and, preferably, an RNA virus such as a retrovirus. The use of viral vectors for gene transfer is well known in the art. For example, a retroviral vector capable of infecting both dividing and non-dividing cells is described in U.S. Pat. No. 6,013,516, which is hereby incorporated by reference. Alternatively, the cells may be transfected using formulations of liposomes comprising nucleic acid encoding the stable HIF-1α variant, as described, for example, in Ledley et al. (1987. J. Pediatrics 110: 1), which is hereby incorporated by reference.

In a further embodiment the naked nucleic acid encoding a stable HIF-1α variant is transfected directly into the desired cells. For example, a matrix comprising the nucleic acid may be placed on the wound where it is taken up and expressed by the cells in the area. Such an approach is described in U.S. Pat. No. 5,962,427, which is hereby incorporated by reference. Nucleic acid encoding a stable HIF-1α variant may also be transfected into cells by use of a "gene gun," as described, for example, in Australian Patent No. 9068389.

In another embodiment cells are transfected ex vivo with nucleic acid encoding a stable HIF-1α variant such that they express the variant polypeptide. The cells are then placed in or near the wound to accelerate wound healing. The cells may be cells that have been removed from the mammal to be treated ("autologous cell trasnfer"). Alternatively, they may be cells from another host or cells that have been maintained in culture. In vitro transfection of cells is well known in the art and may be done, for example, by electroporation, calcium-phosphate precipitation, DEAE-dextran transfection, liposome mediated DNA transfer or transduction with recombinant viral vectors.

In the methods described herein, a subject to be treated can be any mammal, so long as the mammal has a wound that is in need of healing. In a preferred embodiment the subjects are human subjects. However, the present methods may also find particular use in the treatment of wounds in domestic animals.

The types of wounds that may be treated are not limited in any way. A "wound" is any internal or external bodily injury or lesion. Wounds may be caused, for example, by mechanical, chemical, or thermal means, or as the result of a disease or disorder. A wound typically disrupts the normal continuity of one or more bodily structures. Wounds include, without limitation, wounds in which the skin is unbroken (contusions), wounds in which the skin is broken by a cutting instrument (incisions) and wounds in which the skin is broken by a dull or blunt instrument (lacerations). Wounds may be caused by accidents or by intentional acts such as surgical procedures. Wounds may also result from, or be related to a disease or disorder. For example, the wounds may be related to diabetes or cancer. The invention is particularly useful in the treatment of wounds related to diabetes, such as diabetic ulcers.

The methods of the present invention may be used in combination with other conventional therapies for wound healing. In practicing the methods of this invention, the stable HIF-1α variants may be used alone or in combination with other therapeutic or diagnostic agents. In certain preferred embodiments, the compounds of this invention may be co-administered along with other compounds that may be used for the treatment of wounds according to generally accepted medical practice. In one embodiment stable HIF-1α is combined with or administered in concert with other factors that may be useful in accelerating wound healing, such as growth factors, including but not limited to VEGF and FGF. In another embodiment the stable HIF-1α variant can be administered in combination with analgesic drugs used during the treatment of pain that accompanies the wound to be treated.

In one embodiment, a patient suffering from both peripheral vascular disorders and wounds related thereto, such as diabetic ulcers, is treated with stable HIF-1α variants. The wounds are directly contacted with one or more stable HIF-1α variants while the peripheral vascular disorders are treated by expressing the stable HIF-1α variant in the peripheral tissues to stimulate angiogenesis.

Therapeutic formulations of stable HIF-1α are prepared by mixing stable HIF-1α having the desired degree of purity, preferably essentially pure, with optional physiologically acceptable carriers, excipients or stabilizers (Remington's Pharmaceutical Sciences, supra), in the form of lyophilized cake or aqueous solutions. Acceptable carriers, excipients or stabilizers are nontoxic to the cell or mammal being exposed at the dosages and concentrations employed. Examples include buffers such as phosphate, citrate and other organic acids; antioxidants including ascorbic acid; low molecular weight (less than about 10 residues) polypeptides; proteins, such as serum albumin, gelatin or immunoglobulins; hydrophilic polymers such as polyvinylpyrrolidone, amino acids such as glycine, glutamine, asparagine, arginine or lysine; monosaccharides, disaccharides and other carbohydrates including glucose, mannose, or dextrins; chelating agents such as EDTA; sugar alcohols such as mannitol or sorbitol; salt-forming counterions such as sodium; and/or nonionic surfactants such as Tween, Pluronics or PEG.

Stable HIF-1α to be used for in vivo administration is preferably sterile. This is readily accomplished by any method known in the art, such as filtration through sterile filtration membranes, prior to or following lyophilization and reconstitution. Stable HIF-1α may be stored in lyophilized form.

Suitable pharmaceutical formulations are prepared by known procedures using well-known and readily available ingredients. In making the compositions suitable for use in the method of the present invention, the active ingredient will usually be mixed with a carrier, or diluted by a carrier, or enclosed within a carrier. When the carrier serves as a diluent, it may be a solid, semisolid or liquid material that acts as a vehicle, excipient or medium for the active ingredient. Thus, the compositions can be in the form of tablets, pills, powders, lozenges, sachets, cachets, elixirs, suspensions, emulsions, solutions, syrups, aerosol (as a solid or in a liquid medium), soft and hard gelatin capsules, suppositories, sterile injectable solutions and sterile packaged powders for either oral or topical application. Some examples of suitable carriers, excipient, and diluents include lactose, dextrose, sucrose sorbitol, mannitol, starches, gum acacia, calcium phosphates, alginate, tragacanth, gelatin, calcium silicate, microcrystalline cellulose, polyvinylpyrrolidone, cellulose, water syrup, methyl cellulose, methyl and propylhydroxybenzoates, talc, magnesium stearate and mineral oil.

The formulations can additionally include lubricating agents, wetting agents, emulsifying and suspending agents, preserving agents, sweetening agents or flavoring agents. The compositions of the invention may be formulated so as to provide quick, sustained or delayed release of the active ingredient after administration to the patient.

The pharmaceutical preparations comprising stable HIF-1α variants are administered to a mammal, preferably to a human patient, in accord with known methods. Thus the agents of the present invention can be administered, for example, via local, oral, parenteral, subcutaneous, intravenous, intramuscular, intraperitoneal, intracerebrospinal, intra-articular, intrasynovial, intrathecal, transdermal, topical, inhalation or buccal routes. In a preferred embodiment they are administered topically to the wound that is to be treated. They may be administered continuously by infusion, by bolus injection or by the use of a topical formulation with a desired release rate. Generally, where the wound permits the agents should be delivered in a site-specific manner. The compositions can also be delivered through a catheter for local delivery at a target site, or via a biodegradable polymer. The compositions may also be complexed to ligands, or antibodies, for targeted delivery of the compositions. The dosage administered will be dependent upon the age, health, and weight of the recipient, kind of concurrent treatment, if any, frequency of treatment, and the nature of the effect desired.

Topical formulations include ointments, creams and gels. Ointments generally are prepared using either (1) an oleaginous base, i.e., consisting of fixed oils or hydrocarbons, such as white petrolatum or mineral oil, or (2) an absorbent base, i.e., consisting of an anhydrous substance or substances that can absorb water, for example anhydrous lanolin. Customarily, following formation of the base, whether oleaginous or absorbent, the active ingredient (compound) is added to an amount affording the desired concentration. Creams are oil/water emulsions. They consist of an oil phase (internal phase), typically comprising fixed oils, hydrocarbons, and the like, such as waxes, petrolatum, mineral oil, and the like, and an aqueous phase (continuous phase), comprising water and any water-soluble substances, such as added salts. The two phases are stabilized by use of an emulsifying agent, for example, a surface active agent, such as sodium lauryl sulfate; hydrophilic colloids, such as acacia colloidal clays, veegum, and the like. Upon formation of the emulsion, the active ingredient (compound) customarily is added in an amount to achieve the desired concentration. Gels typically comprise a base selected from an oleaginous base, water, or an emulsion-suspension base. To the base is added a gelling agent which forms a matrix in the base, increasing its viscosity. Examples of gelling agents are hydroxypropyl cellulose, acrylic acid polymers, and the like. Customarily, the active ingredient (compounds) is added to the formulation at the desired concentration at a point preceding addition of the gelling agent. The amount of compound incorporated into a topical formulation is not critical; the concentration should be within a range sufficient to permit ready application of the formulation to the affected tissue area in an amount that will deliver the desired amount of compound to the desired treatment site. The customary amount of a topical formulation to be applied to an affected tissue will depend upon an affected tissue size and concentration of compound in the formulation.

Suitable formulations for parenteral administration include aqueous solutions of the active compounds in water-soluble form, for example, water-soluble salts. In addition, suspensions of the active compounds as appropriate oily injection suspensions may be administered. Suitable lipophilic solvents or vehicles include fatty oils, for example, sesame oil, or synthetic fatty acid esters, for example, ethyl oleate or triglycerides. Aqueous injection suspensions may contain substances which increase the viscosity of the suspension include, for example, sodium carboxymethyl cellulose, sorbitol, and/or dextran. Optionally, the suspension may also contain stabilizers. Liposomes can also be used to encapsulate the agent. The agent can also be prepared as a sustained-release formulation, including semipermeable matrices of solid hydrophobic polymers containing the protein. The sustained release preparation may take the form of a gel, film or capsule.

Suitable formulations for oral administration include hard or soft gelatin capsules, pills, tablets, including coated tablets, elixirs, suspensions, syrups or inhalations and controlled release forms thereof.

While individual needs vary, determination of optimal ranges of effective amounts of the stable HIF-1α variants is within the skill of the art. The appropriate dosage of agent will depend on the type of wound to be treated, the severity and course of the wound, previous therapy, the patient's clinical history and response to the agent, and the discretion of the attending physician. Therapeutic agents are suitably administered to the patient at one time or over a series of treatments. For repeated administrations over several days or longer, depending on the condition, the treatment is sustained until a desired extent of healing is obtained. The progress of this therapy is easily monitored by conventional techniques and assays.

In another embodiment of the invention, an article of manufacture containing materials useful for the acceleration of wound healing is provided. The article of manufacture comprises a container and a label or package insert(s) on or associated with the container. Suitable containers include, for example, bottles, vials, syringes, etc. The containers may be formed from a variety of materials such as glass or plastic. The container holds a composition that is effective for accelerating wound healing. At least one active agent in the composition is a stable HIF-1α variant. The label or package insert indicates that the composition is used for accelerating wound healing and may provide instructions for such use.

The compositions according to the invention can be administered in any circumstance in which wound healing is desired.

EXAMPLES

Example 1
Transgenic Mice Expressing an HIF-1α Variant

Wild-type human HIF-1α or HIF-1αΔODD cDNA (Huang, L., J. Gu, M. Schau, and H. Bunn. 1998. Proc. Natl. Acad. Sci. U.S.A. 95: 7987–92) was cloned into the SmaI site of a keratin-14 expression vector (FIG. 1a). Briefly, plasmids p(HA)HIF-1α and p(HA)HIF-1α(401Δ603) (HIF-1αΔODD)(Huang, L., J. Gu, M. Schau, and H. Bunn. 1998. Proc. Natl. Acad. Sci. U.S.A. 95: 7987–92) were digested with XbaI and Asp718I to release cDNA inserts, gel purified over QIAquick columns (QIAgen, Valencia, Calif.), blunted with Klenow polymerase and blunt-end cloned into a SmaI-linearized K14 expression cassette (Munz, B. et al. 1999. EMBO Journal 18: 5205–5215). Plasmid DNA was prepared with QIAgen Endofree Plasmid Maxi Kit. Entire transgene inserts were liberated from vector by Asp718I digestion, purified and electroeluted from acrylamide gels (Arbeit, J. et al. 1994. Journal of Virology 68: 4358–68).

Microinjection into embryos of the FVB/n in-bred mouse strain produced eight K14-HIF-1α and five K14-HIF-1αΔODD transgenic founder mice, as confirmed by PCR of tail DNA. Transgene copy number ranged from 2–20 in heterozygous founder mice and all subsequent work was performed in heterozygous transgenic mice and non-transgenic controls. RT-PCR analysis of total RNA from ear skin demonstrated transgene expression in six HIF-1α, and all five HIF-1αΔODD transgenic founders. In situ hybridization revealed that transgene mRNA was appropriately targeted to basal keratinocytes of the interfollicular epidermis as well as the hair follicle outer root sheath, and confirmed that transgene expression was similar in mice containing either wild-type or HIF-1αΔODD cDNA (FIG. 1d). Endogenous murine HIF-1α was undetectable in non-transgenic skin (Elson, D. et al. Cancer Research 60: 6189–6195).

By 1–2 months of age all five K14-HIF-1αΔODD transgenic founders developed a distinctive skin phenotype consisting of prominent reddening and vasculature of unfurred skin, including the ears (FIG. 1b, right panel), paws, and tails. In addition, the coat of truncal skin was roughened and uneven (FIG. 1b). Ears of each K14-HIF-1α transgenic founder mouse had the usual pink-white color of nontransgenic littermates (FIG. 1b middle and left panels, respectively).

Three lines expressing mutant human HIF-1αΔODD derived from founder numbers #19, 62, and 71 that demonstrated similarly affected skin, and two lines expressing wild type human HIF-1α, founder #'s 23 and 49 were established based on the initial RT-PCR expression analysis. Subsequent quantitative RT-PCR using SYBR green detection revealed that transgene expression differences between the three lines varied according to #19>#71>#62, which was similar to the copy number differences between these lines (approximately 20, 4, and 1–2 respectively). Subsequent work revealed a subtle difference in intensity of skin redness between the K14-HIF-1αΔODD transgenic lines. However, blood vessel biology defined by vascular density and blood vessel leakage resistance was similar in the three K14-HIF-1αΔODD transgenic lines regardless of copy number and transgene expression level. Mice transgenic with wild-type human HIF-1α cDNA were analyzed together, as transgene expression was similar within these two established lines, and neither line displayed a visible or histological phenotype.

Example 2
Skin Histopathology in HIF-1α Transgenic Mice

Histopathological analysis of both furred and unfurred skin was performed. Briefly, five micron sections of paraformaldehyde fixed, paraffin embedded tissue were cut and stained with hematoxylin and eosin (Sigma, St Louis, Mo.) for histopathological analysis. mRNA in-situ hybridization was performed using $^{35}S$ radiolabeled cRNA riboprobes as described previously (Arbeit, et al. 1996. Oncogene 13: 1847–57). A riboprobe complementary to human HIF-1α cDNA was used for transgene expression, whereas riboprobes complementary to mouse VEGF and GLUT-1 were used for HIF-1 target gene expression (Arbeit, et al. 1996. Oncogene 13: 1847–57).

Analysis of ear (FIG. 1c) and back skin from K14-HIF-1αΔODD transgenic mice indicated an increased number of dermal blood vessels immediately below the epidermis and surrounding the hair follicles (see arrowheads FIG. 1c). Neither edema, nor inflammation was detectable in dermis or epidermis of K14-HIF-1αΔODD transgenic mice, and the epidermis itself was indistinguishable from nontransgenic mice (FIG. 1c). Lack of edema or inflammation in K14-HIF-1αΔODD transgenic mice was notable because VEGF, a HIF-1 target gene induced in these transgenic mice (FIG. 2), produces both pathologies when either the 164 or 120 isoform was overexpressed in basal keratinocytes of K14-VEGF164 or bovine K6-VEGF120 transgenic mice (Detmar, M. et al. 1998. Journal Investigative Dermatology 111: 1–6) (Thurston, G., C. Suri, K. Smith, J. McClain, T. Sato, G. Yancopoulos, and D. McDonald. 1999. *Science* 286: 2511–2514) (Larcher, et al. 1998. Oncogene 17: 303–311).

Groups of K14-HIF-1αΔODD and K14-HIF-1α transgenic mice and non-transgenic littermates were observed and serially sacrificed up to 18 months of age. While skin redness in the K14-HIF-1αΔODD transgenic mice was greater by 2–3 months of age, ulceration, angioma formation, or spontaneous skin tumor did not develop during more prolonged observation. K14-HIF-1α transgenic mice remained phenotypically indistinguishable from non-transgenic littermates during the same duration of observation. In contrast, the skin phenotype of K14-VEGF164 transgenic mice was progressive such that spontaneous hemorrhagic ulcers developed in older mice (Thurston, G., C. Suri, K. Smith, J. McClain, T. Sato, G. Yancopoulos, and D. McDonald. 1999. *Science* 286: 2511–2514). It is also surprising that skin inflammation was not produced in K14-HIF-1α∆ODD transgenic mice given the ability of VEGF164 (FIG. 5) to increase leukocyte adherence and extravasation when overexpressed in skin (Detmar, M. et al. 1998. Journal Investigative Dermatology 111: 1–6).

Example 3

Analysis of HIF-1 Target Gene Expression in HIF-1α Transgenic Mice

Figure 2:
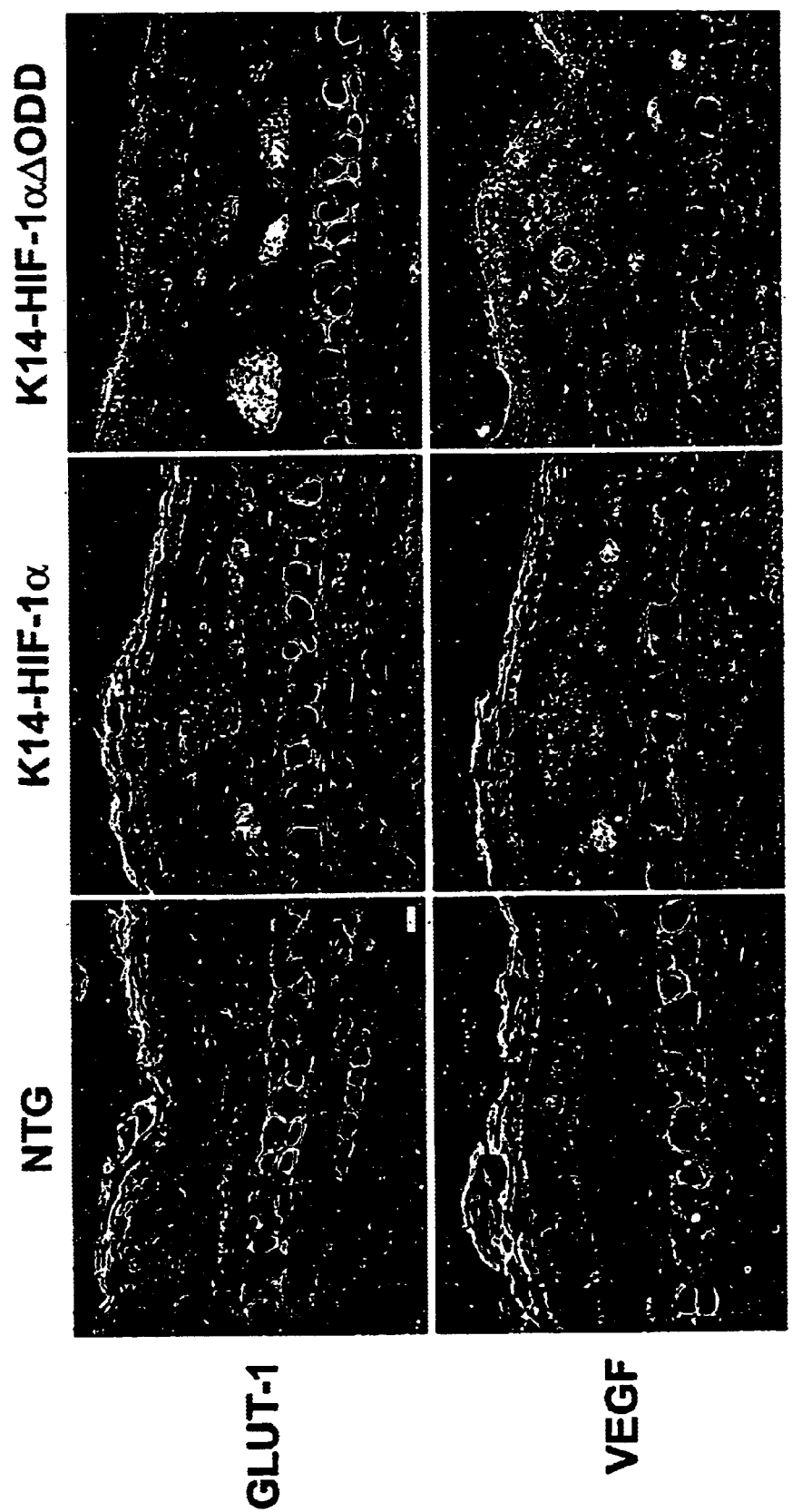
FIG. 2. Expression of HIF-1 target genes. Glucose transporter-1 (GLUT-1) and vascular endothelial growth factor (VEGF) are expressed in both interfollicular epidermis and in the hair follicle outer root sheath of K14-HIF-1αΔODD transgenic mice. Low-level signals for both GLUT-1 and VEGF are present in the hair follicle outer root sheath of K14-HIF-1α transgenic mice, whereas neither target gene is detectable in ear skin of nontransgenic mice. Bar, 20 μm.

Since the sequence of human and mouse HIF-1α cDNA's are >90% conserved at the amino acid level (Semenza, G. 1999. *Annual Review Cell and Development Biology* 15: 551–78.), overexpressed human protein would be expected to heterodimerize with endogenous mouse HIF-1β/ARNT to form a functional HIF-1 transcription factor. The transcriptional activity of HIF-1 produced in skin of K14-HIF-1α∆ODD and K14-HIF-1α transgenic mice was determined by monitoring expression of two of its downstream targets, glucose transporter-1 (GLUT-1) and VEGF, using mRNA in situ hybridization. Both GLUT-1 and VEGF mRNA were easily detectable in both the interfollicular epidermis and hair follicles of K14-HIF-1α∆ODD transgenic mice (FIG. 2). The strong induction of HIF-1 target genes that was observed underscores the use of the ∆ODD mutant compared to the wild type cDNA as a means to bypass protein degradation and insure gain of HIF-1α function.

Figure 3:
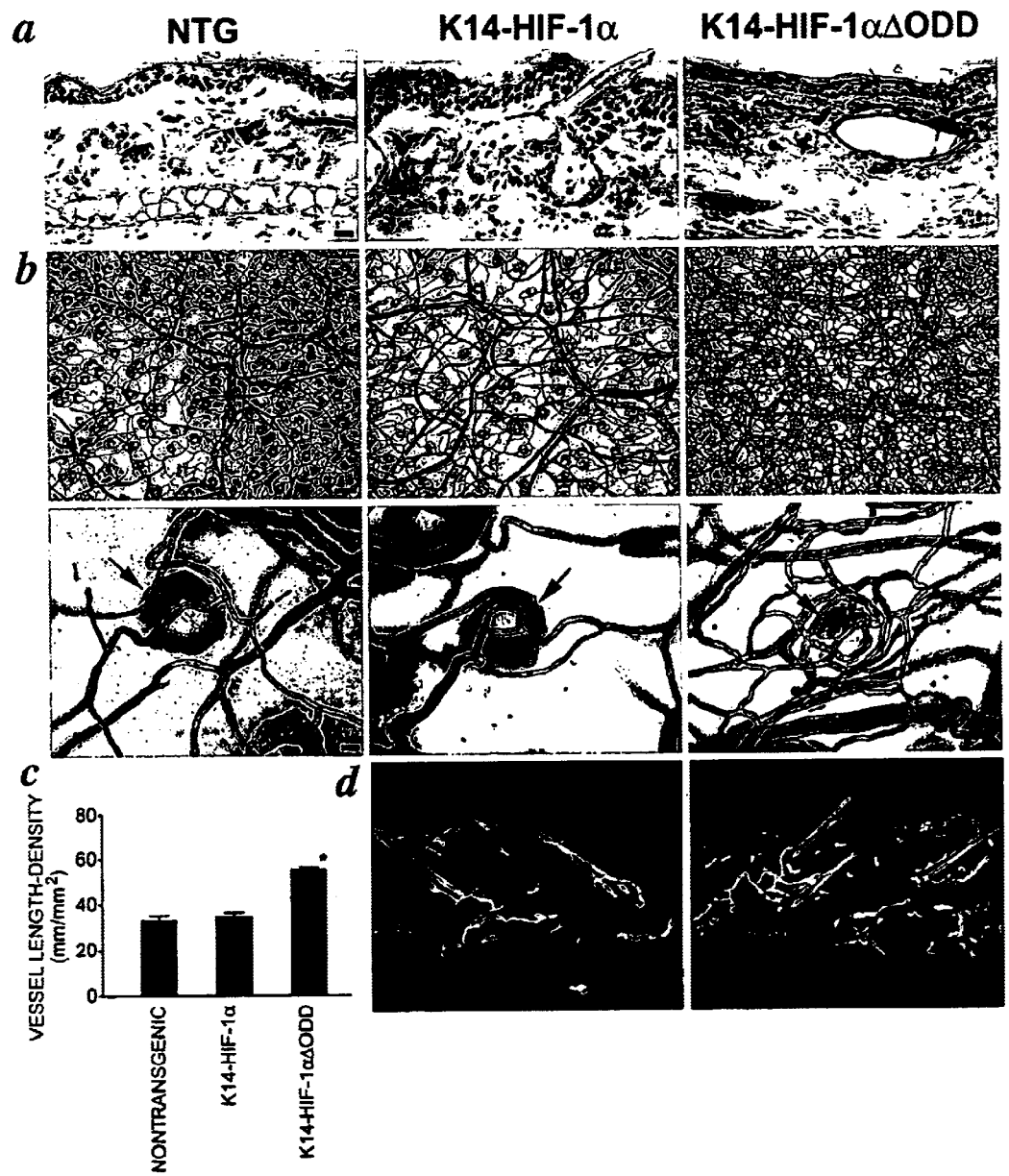
FIG. 3. Blood vessel location, distribution, and permeability. (a) Immunohistochemistry for CD31 expression demonstrates an increase in the number of dermal capillaries beneath the epidermis in the K14-HIF-1αΔODD compared to either the K14-HIF-1α transgenic mice or nontransgenic controls. (b) Blood vessel morphology and multiplicity revealed by perfusion with biotinylated *Lycopersicon esculentum* lectin (Thurston, G., C. Suri, K. Smith, J. McClain, T. Sato, G. Yancopoulos, and D. McDonald. 1999. *Science* 286: 2511–2514). Low power views demonstrate the marked increase in blood vessel density in the K14-HIF-1αΔODD transgenic mice. High power views reveal that this increase is predominantly due to an increase in capillaries with normal morphology. Capillaries and small caliber vessels are concentrically arranged around hair follicles in the K14-HIF-1αΔODD transgenic mice. The hair follicle sebaceous glands are peroxidase positive because of endogenous biotin (black arrows each lower panel in b). (c) Quantification of microvasculature vessel length-density (Thurston, G., C. Suri, K. Smith, J. McClain, T. Sato, G. Yancopoulos, and D. McDonald. 1999. *Science* 286: 2511–2514) from lectin perfused ears confirm a 66% increase in blood vessel number in the K14-HIF-1αΔODD transgenic mice compared to either K14-HIF-1α or nontransgenic mice (*P<0.05, Mann-Whitney U test). Eight 10×fields from two to six mice of each genotype were counted. (d) Fluorescent lectin staining in thick sections shows that hair follicles and interfollicular epidermis in back skin of K14-HIF-1αΔODD transgenic mice (right panel) are decorated with small blood vessels, whereas nontransgenic back skin (left panel) contains only sporadic microvessels in the same locations. Bars, (a) and lower line (b) 20 μm, upper line (b) 150 μm.

In contrast, no VEGF or GLUT-1 expression was detectable in the interfollicular epidermis of transgenic mice overexpressing wild-type human HIF-1α cDNA. However, low-level signal for both HIF-1 targets was present in the hair follicles (FIG. 2). Hair follicles may be a niche where HIF-1α protein is functional at low levels, because they are the site of cyclical proliferation controlled by paracrine growth factors (Gat, et al. 1998. Cell 95: 605–614), and wild-type HIF-1α protein is stabilized by growth factor signaling in addition to hypoxia (Feldser, D. et al. 1999. Cancer Research 59: 3915–3918). This low-level induction of VEGF mRNA is insufficient to produce a hypervascular phenotype in the K14-HIF-1α transgenic mice (FIGS. 1b and 3a). Lack of expression of HIF-1 targets in non-transgenic skin is further evidence for the undetectable level of endogenous murine HIF-1α activity in epidermis (FIG. 2).

Example 4

Analysis of Blood Vessel Multiplicity in HIF-1α Transgenic Mice

Immunohistochemistry with an antibody recognizing the endothelial marker CD31 indicated an increase of dermal blood vessels immediately below the epidermis in the ears of K14-HIF-1α∆ODD transgenic mice (FIG. 3a). Ten micron frozen tissue sections were mounted on Superfrost Plus slides (Fisher Scientific, Pittsburgh, Pa.), air dried, fixed in acetone at 4° C. for 10 min., air dried again, and washed in 1×PBS. Sections were blocked in a combined solution of 5% normal goat serum (Cappel-Organon Teknika, Durham, N.C.)/3% bovine serum albumin/2% fish gelatin (both from Sigma) in PBS for 30 min. at 25° C., pre-incubated with Avidin solution for 15 min, followed by biotin for 15 min (Avidin-Biotin Blocking Kit, Vector Laboratories, Burlingame, Calif.). Sections were then incubated with biotinylated rat anti-mouse CD31 monoclonal antibody (Pharmingen, San Diego, Calif.), diluted 1:2500 in blocking buffer, overnight at 4° C., followed by serial incubation with a biotinylated goat anti-rat IgG (Pierce, Rockford, Ill.), ABC Alkaline Phosphatase Standard solution (Vector), and BCIP/NBT Alkaline Phosphatase Substrate Kit IV (Vector). Sections were counterstained with nuclear fast red (Vector). Vessel density per unit area was quantified from three random 40× fields using a Chalkley reticule. Statistical significance was determined using the Mann-Whitney U test (GraphPad Prism, San Diego, Calif.).

The Chalkley analysis of vascular density in ear skin (Chalkley, H. 1943. Journal National Cancer Institute 4: 47–53) revealed a statistically significant 30% increase in number of blood vessels in the K14-HIF-1α∆ODD transgenic mice compared to either the K14-HIF-1α transgenic counterparts or non-transgenic controls, which were similar to each other.

To characterize blood vessel morphology and delineate blood vessel number and distribution in three dimensions, and to determine whether flow was present within individual vessels, the vasculature of transgenic and non-transgenic mice was stained by intravenous injection of biotinylated *Lycopersicon esculentum* lectin prior to perfusion-fixation. Transgenic and non-transgenic mice 8–12 weeks of age were anesthetized and injected intravenously via the femoral vein with biotinylated *Lycopersicon esculentum* lectin (Vector), 100 µg/mouse, followed by perfusion through the aorta with 1% paraformaldehyde+0.5% glutaraldehyde, pH 7.4. Ears were removed, skin separated from cartilage, and stained with ABC (peroxidase) and 3,3'-diaminobenzidine. Vessel length-density was determined using a computerized algorithm (Thurston, G., C. Suri, K. Smith, J. McClain, T. Sato, G. Yancopoulos, and D. McDonald. 1999. *Science* 286: 2511–2514). For fluorescent visualization, mice were injected with fluoresceinated lectin (Vector), 120 µg/mouse, followed by perfusion with 1% paraformaldehyde, pH 7.4. Ears were dissected and embedded in tissue freezing medium, cut in 40 µm sections, mounted and visualized by epifluorescence.

Low power views of ear skin whole mounts further demonstrated the marked increase in number of perfused blood vessels in K14-HIF-1α∆ODD transgenic mice compared to either K14-HIF-1α counterparts or non-transgenic controls, which again were similar to each other (FIG. 3b). High power views revealed that blood vessels with a diameter and morphology consistent with capillaries were predominantly increased the K14-HIF-1α∆ODD transgenic mice, whereas the number and distribution of large caliber vessels appeared similar in all groups (FIG. 3b). Quantification of vascularity using a length-density algorithm (Thurston, G., C. Suri, K. Smith, J. McClain, T. Sato, G. Yancopoulos, and D. McDonald. 1999. *Science* 286: 2511–2514) revealed a 66% increase in blood vessel length-density in all lines of K14-HIF-1α∆ODD transgenic mice compared to non-transgenic controls (FIG. 3c). Vessel length-density in K14-HIF-1α transgenic mice was similar to non-transgenic controls.

Blood vessel multiplicity and distribution in back skin was investigated by perfusion of K14-HIF-1α∆ODD and non-transgenic mice with a fluorescein labeled *L. esculentum* lectin. Thick frozen sections were used for microscopic analysis (FIG. 3d). Interfollicular epidermis and hair follicles were extensively decorated with small caliber capillary-like blood vessels in the K14-HIF-1α∆ODD transgenic mice (FIG. 3d, right panel). In contrast, there were only occasional small caliber capillary-like blood vessels adjacent to hair follicles and only rare interfollicular blood vessels evident in the non-transgenic mice (FIG. 3d, left panel). Induction of an extensive microvasculature by HIF-1αΔODD was consistent with pronounced upregulation of VEGF expression. However, capillaries developing in K14-HIF-1αΔODD transgenic mice were morphologically similar to those of non-transgenic mice. These microvessels lacked the tortuosity of microvasculature induced in mice overexpressing VEGF164 (Thurston, G., C. Suri, K. Smith, J. McClain, T. Sato, G. Yancopoulos, and D. McDonald. 1999. *Science* 286: 2511–2514), or the saccular morphology of vessels produced in transgenic mice overexpressing angiopoietin-1 (Suri, C. et al. 1998. Science 282: 468–471).

Example 5
Determination of Blood Vessel Permeability in HIF-1α Transgenic Mice

A hallmark of VEGF activity is its ability to increase blood vessel permeability (Dvorak, H. et al. 1999. Current Topics in Microbiology and Immunology 237: 97–132). The inherent leakiness of the microvasculature of transgenic mice overexpressing either VEGF164 or VEGF120 is consistent with this VEGF function (Thurston, G., C. Suri, K. Smith, J. McClain, T. Sato, G. Yancopoulos, and D. McDonald. 1999. *Science* 286: 2511–2514) (Larcher, et al. 1998. Oncogene 17: 303–311). Given the induction of VEGF mRNA by transgene expression (FIG. 2), a similar increase in blood vessel permeability would be expected in K14-HIF-1αΔODD transgenic mice. To test for leakiness, transgenic and non-transgenic mice 8–12 weeks of age were anesthetized (ketamine/xylazine) and injected intravenously with Evans blue dye, 30 mg/kg/mouse. The right ear was treated twice over 30 min. with mustard oil (5% in heavy mineral oil) (Sigma, St. Louis, Mo.). Mice were perfused through the aorta with 1% paraformaldehyde in citrate buffer, pH 3.5. Ears were dissected and weighed. Extravasated dye was extracted with formamide and quantified with a spectrophotometer (610 nm).

Figure 4:
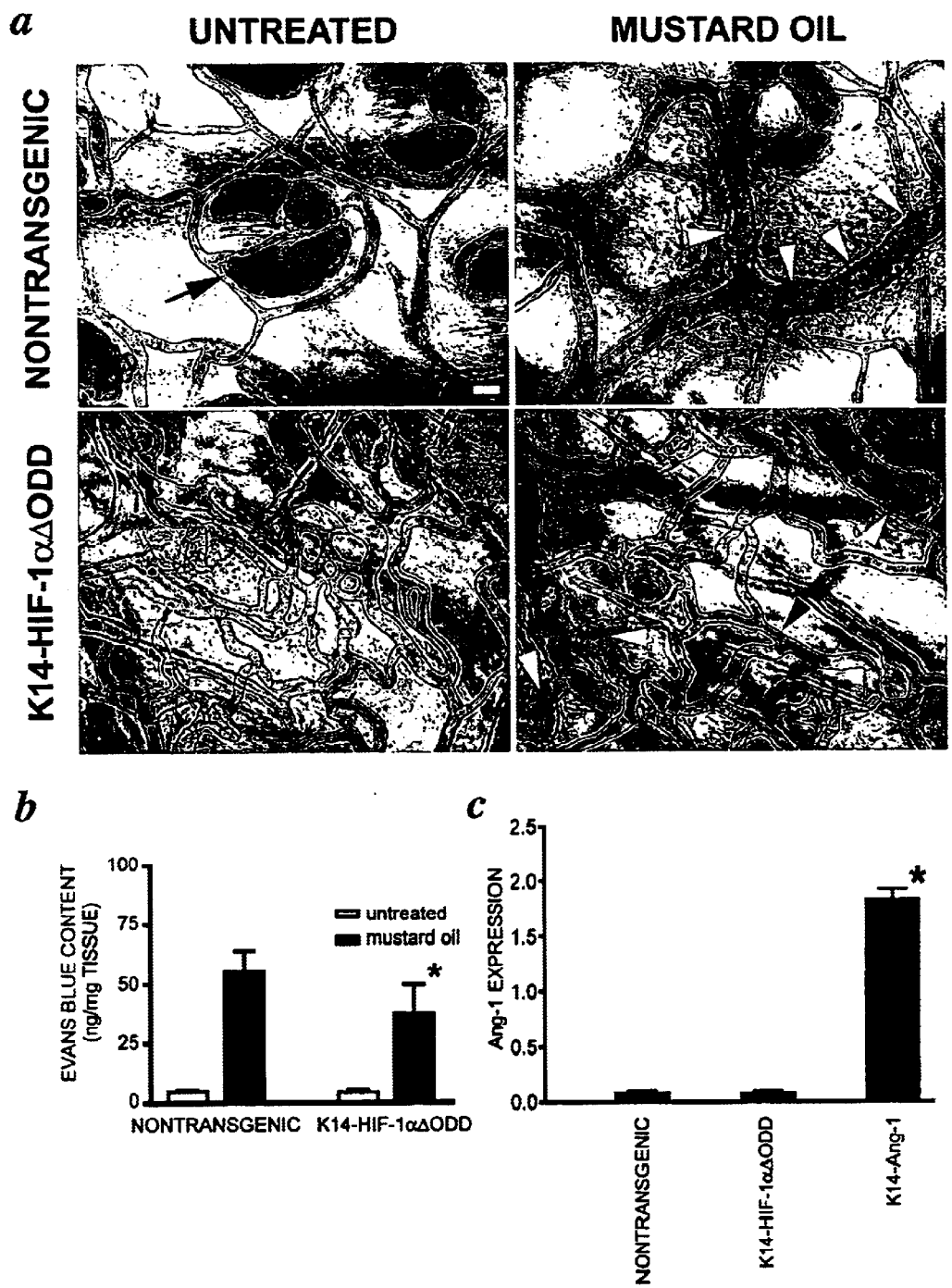
FIGS. 4a–4c. Determination of leakage sites and quantification of leak. (a) Mice were perfused with biotinylated *Ricinus communis* I lectin which binds to endothelial basement membrane exposed at sites of vascular leak (Thurston, G., P. Baluk, A. Hirata, and D. McDonald. 1996. American Journal of Physiology 271: H2547–2562). Neither K14-HIF-1αΔODD nor nontransgenic mice evidence vascular leak at baseline (left upper and lower panels) despite blood vessel exposure to 6–10-fold elevations of VEGF and a marked increase in dermal capillaries in the K14-HIF-1αΔODD transgenic mice. Following mustard oil application, sites of intense leakage are predominantly located at relatively large caliber postcapillary venules (white arrowheads) compared to capillary-like vessels (black arrowheads) in both the K14-HIF-1αΔODD transgenic mice and nontransgenic controls (right upper and lower panels). Leak from postcapillary venules appeared more intense in the nontransgenic compared to the K14-HIF-1αΔODD transgenic mice. (Arrow indicates a normal sebaceous gland) Bar, 20 μm. (b) Ear Evans blue dye content 30 minutes post intravenous injection of K14-HIF-1αΔODD transgenic mice and nontransgenic controls. There is absence of baseline leak in both transgenic and nontransgenic mice, and a significantly lower leak in the mustard oil treated ear, four to six mice analyzed per group (*P<0.05, Mann-Whitney U test). (c) Real-time TaqMan RT-PCR analysis of angiopoietin-1 (Ang-1) expression from total RNA isolated from ears of K14-Ang-1, K14-HIF-1αΔODD transgenic mice and nontransgenic controls, using histone 3.3A as a reference (25). Three mice of each genotype were analyzed (*P<0.05, Mann-Whitney U test).

Surprisingly, baseline vascular leakage in untreated K14-HIF-1αΔODD transgenic mice was similar to that of non-transgenic controls following Evans blue dye injection (FIG. 4). Moreover, in response to inflammatory stimulation with topical mustard oil, skin vessels in K14-HIF-1αΔODD transgenic mice displayed a modest but significantly lower level of blood vessel leakage compared to non-transgenic controls (FIG. 4b). In contrast, transgenic mice overexpressing VEGF164 displayed elevated vascular leak at baseline that further increased following inflammatory stimuli (Thurston, G., C. Suri, K. Smith, J. McClain, T. Sato, G. Yancopoulos, and D. McDonald. 1999. *Science* 286: 2511–2514). The baseline and inflammatory vessel leakage in K14-HIF-1α transgenic mice was similar to non-transgenic controls. Thus, despite induction of VEGF and an increase in microvascular density, HIF-1α overexpression produces a vasculature that is non-leaky at baseline, in the absence of an exogenous stimulus, and leakage resistant in response to acute inflammation.

Evans blue dye content is a measurement of vascular permeability across an entire tissue sample but does not examine leakage at individual blood vessels. To investigate the mechanism of leakage resistance suggested by the Evans blue dye analysis, mice were perfused with biotinylated *Ricinus communis* I lectin (FIG. 4a). Ricin weakly binds to intact vascular endothelium, but avidly adheres to vascular basement membrane exposed at sites of leakage, and also diffuses out into the perivascular space, staining tissue in the vicinity of blood vessels (Thurston, G., C. Suri, K. Smith, J. McClain, T. Sato, G. Yancopoulos, and D. McDonald. 1999. *Science* 286: 2511–2514). Thus ricin allows determination of the number of leaky sites across the vasculature, and also permits a qualitative assessment of the extent of leakage in individual vessels. Ricin staining was carried out using a similar protocol to that described above for Evans blue dye. Under anesthesia, 5% mustard oil was applied topically to one ear. Twenty minutes later, mice were perfused with fixative (1% paraformaldehyde plus 0.5% glutaraldehyde), and the vasculature was stained by perfusion of biotinylated ricin lectin, 200 µg/mouse (*Ricinus communis* I, Vector). Ears were removed, the skin dissected from the cartilage as a whole mount, and the lectin visualized by reaction with avidin peroxidase and diaminobenzidine substrate.

Ricin perfusion of untreated ears failed to demonstrate leaky sites in either K14-HIF-1αΔODD or non-transgenic mice (FIG. 4a). These results are consistent with the lack of baseline leak evident in the untreated K14-HIF-1αΔODD transgenic mice in the Evans blue dye study (FIG. 4b).

In response to mustard oil, both K14-HIF-1αΔODD and non-transgenic mice displayed numerous leaky sites after treatment (FIG. 4a). Leaky sites were predominantly located in postcapillary venules (FIG. 4a, white arrowheads), compared to capillaries (black arrowhead). The intensity of leak at postcapillary venules was less in the K14-HIF-1αΔODD transgenic mice compared to the non-transgenic controls treated with mustard oil and likely accounted for the statistically significant decrease in Evans blue content. Thus, despite marked induction of VEGF (FIG. 2) the extensive microvasculature induced by HIF-1α overexpression is leakage-resistant at baseline. However, the microvasculature retains its permeability response during inflammation with a modest decrease in postcapillary venular leak. These results indicate that blood vessels induced by HIF-1α retain the properties of non-transgenic vasculature in contrast to the microvasculature induced when VEGF164 or VEGF120 are overexpressed in basal keratinocytes (Thurston, G., C. Suri, K. Smith, J. McClain, T. Sato, G. Yancopoulos, and D. McDonald. 1999. *Science* 286: 2511–2514) (Larcher, et al. 1998. Oncogene 17: 303–311).

Example 6
Analysis of Angiopoietin-1 and -2 Expression in HIF-1α Transgenic Mice The property of leakage-resistance resembles the baseline microvascular phenotype of transgenic mice overexpressing angiopoietin-1 (Ang1) (Thurston, G., C. Suri, K. Smith, J. McClain, T. Sato, G. Yancopoulos, and D. McDonald. 1999. *Science* 286: 2511–2514). As leakage-resistance induced by angiopoietin-1 is dominant over VEGF mediated increase in permeability (Thurston, G., C. Suri, K. Smith, J. McClain, T. Sato, G. Yancopoulos, and D. McDonald. 1999. *Science* 286: 2511–2514), the involvement of angiopoietins in the lack of baseline leak of the microvasculature induced by HIF-1α overexpression was investigated. To determine whether Ang-1 or Ang-2 expression, also upregulated by hypoxia (Oh, H. et al. 1999. Journal of Biological Chemistry 274: 15732–15739), were coordinately increased by HIF-1α overexpression, real-time RT-PCR was carried out using PCR primers and TaqMan probes specific for Ang-1 and Ang-2. Relative expression levels were calculated as detailed previously (Ginzinger, D. et al. Cancer Research 60: 5405–5409). Briefly, relative expression was calculated as $2^{-(ctVEF\ isoform-Ct\ histone\ 3.3A)}$ using histone 3.3A as an endogenous control gene.

Ang-1 was expressed at the same low level in ears from both K14-HIF-1αΔODD transgenic mice and non-transgenic controls (FIG. 4c), compared to a 20-fold elevation of expression detected in ears of K14-Ang-1 transgenic mice (FIG. 4c). Similarly, Ang-2 was expressed at low levels in K14-HIF-1αΔODD transgenic mice and non-transgenic controls. In contrast, Ang-2 was expressed at 45-fold greater level in total RNA from positive control tissue, placenta of day 14 non-transgenic mouse embryos.

Parallel mRNA in-situ hybridization analysis of Ang-1 and Ang-2 expression was performed in ear skin obtained from K14-HIF-1α and K14-HIF-1αΔODD transgenic mice and compared to Ang-1/Ang-2 expression in day 11–13 embryos. There was no detectable hybridization signal for either Ang-1 or Ang-2 in transgenic or non-transgenic ear skin, compared to a strong signal in embryonic atria, aorta, and somites.

Example 7

Analysis of VEGF Expression in HIF-1α Transgenic Mice

Figure 5A:
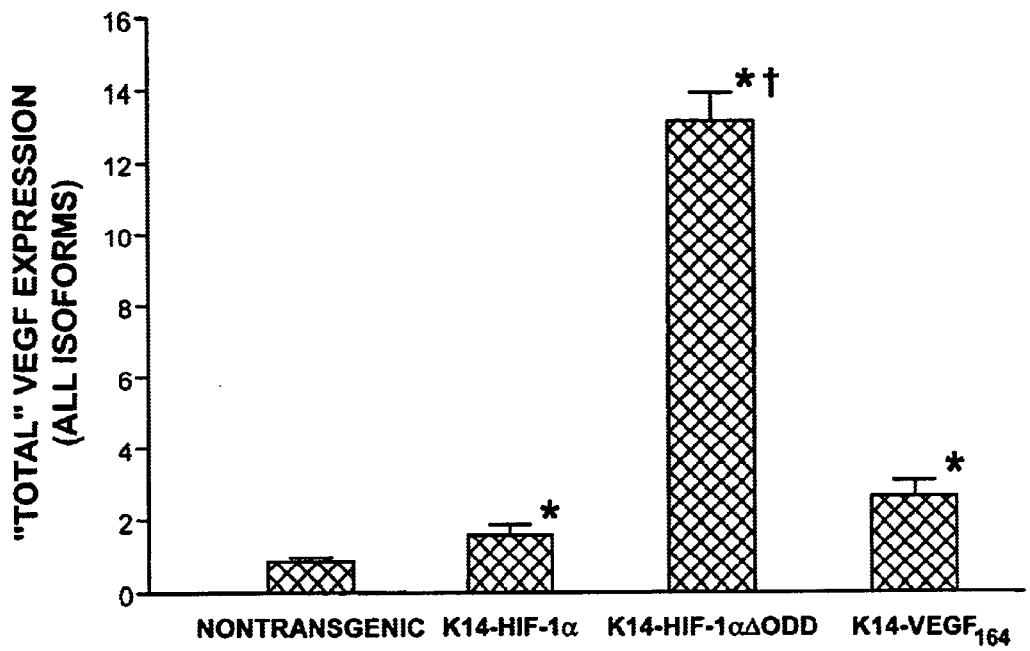
FIGS. 5a–5d. Expression of total VEGF and VEGF isoforms. (a) Real-time RT-PCR determination of total VEGF isoform expression in ear skin of K14-HIF-1α, K14-HIF-1αΔODD and K14-VEGF164 transgenic mice and nontransgenic controls. Three mice from each genotype were analyzed, and VEGF mRNA levels are calculated relative to histone 3.3A in each sample. Total VEGF mRNA levels are increased 80% in K14-HIF-1α transgenic mice compared to nontransgenic controls (*P=0.02, Student's t-test). Total VEGF mRNA is elevated 13-fold in K14-HIF-1αΔODD transgenic mice compared to nontransgenic controls (*P<0.0001, Student's t-test), and 4-fold compared to K14-VEGF164 transgenic mice (†P=0.0003, Student's t-test). Total VEGF is elevated 2-fold in ear skin from K14-VEGF164 transgenic mice compared to nontransgenic controls (*P=0.02, Student's t-test). (b) Real-time RT-PCR determination of VEGF isoform expression in ear skin of nontransgenic controls and K14-HIF-1αΔODD and K14-VEGF164 transgenic mice. PCR primers flanking each indicated isoform and fluorescent TaqMan probes specific for each splice junction were used in the analysis (Tober, K., et al. 1998. Biochemical and Biophysical Research Communications 247: 644–653). VEGF isoforms in each sample were calculated with histone 3.3A as a reference. Triplicate determinations performed and the mean used in calculations. Three to four mice were analyzed in each group (*P<0.05, compared to level of nontransgenic controls, Mann-Whitney U test; †P<0.05 pattern of expression different from nontransgenic, ANOVA with maximum likelihood test). (c) Calculation of the fold induction of each VEGF isoform in K14-HIF-1αΔODD and K14-VEGF164 transgenic mice compared to nontransgenic controls. There is an equivalent 6–10 fold induction of each VEGF isoform in the K14-HIF-1αΔODD transgenic mice while only the 164 isoform is increased in K14-VEGF164 transgenic mice. The pattern of VEGF isoform induction is significantly different in the two groups of transgenic mice (*P<0.05, ANOVA with maximum likelihood test). (d) VEGF protein levels in transgenic and nontransgenic mice. ELISA analysis of protein extracts from ear skin demonstrates a 0.5- to 3-fold increase of VEGF protein in the three separate K14-HIF-1αΔODD transgenic mouse lines (#'s 62, 19, and 71 in order of magnitude), and a 2-fold increase in heterozygousK14-VEGF164 transgenic mice, compared to nontransgenic controls and K14-HIF-1α transgenic mice (*p<0.05, Student's t-test).

One explanation for the absence of baseline vascular leak in K14-HIF-1αΔODD transgenic mice compared to overt leakage in transgenic mice overexpressing VEGF164 or 121(Thurston, G., C. Suri, K. Smith, J. McClain, T. Sato, G. Yancopoulos, and D. McDonald. 1999. *Science* 286: 2511–2514) (Larcher, et al. 1998. Oncogene 17: 303–311), was that constitutive HIF-α overexpression induced lower levels of VEGF expression compared to direct transgenic expression of VEGF cDNA from a keratin-14 promoter. To test this possibility, real-time RT-PCR was performed using PCR primers amplifying exons 3 and 4 of the mouse VEGF-A gene, which are common to all VEGF-A isoforms (Tober, K., et al. 1998. Biochemical and Biophysical Research Communications 247: 644–653), along with a TaqMan probe specific for the exon 3/4 splice junction. Quantitative RT-PCR was performed on total RNA isolated from heterozygous K14-VEGF164, K14-HIF-1αΔODD and K14-HIF-1α transgenic mice, along with non-transgenic littermate controls. In contrast to in-situ hybridization, the increased sensitivity of real-time RT-PCR detected a signal for VEGF mRNA in non-transgenic ear. Total VEGF mRNA levels were elevated 80% in K14-HIF-1α transgenic mice (FIG. 5a), and 8- to 13-fold in the K14-HIF-1αΔODD transgenic mouse lines compared to non-transgenic controls (FIG. 5a). The levels of VEGF mRNA demonstrated in ear skin of K14-HIF-1αΔODD transgenic mice is similar to the 13–25-fold elevation of VEGF expression produced by hypoxia in cultured cells (Ikeda et al. 1995; Levy et al. 1995; Levy et al. 1996b; Stein et al. 1998). HIF-1αΔODD mediated VEGF mRNA induction is within range, although higher, than the 2.5–8-fold increased in VEGF mRNA levels in hypoxic tissues (Banai et al. 1994; Lee et al. 1999; Miraliakbari et al. 2000) (REF). These differences may be due to sensitivity of the real-time RT-PCR used here, compared to Northern analysis used in prior work.

Parallel analysis of total VEGF expression in skin squamous cancers in transgenic mice expressing HPV16 oncogenes revealed a 20–30 fold increase in VEGF mRNA (data not shown), indicating that VEGF expression in the K14-HIF-1αΔODD transgenic mice was not supraphysiologic. Surprisingly, total VEGF mRNA levels were only elevated 2-fold in K14-VEGF164 transgenic mice that were heterozygous for the transgene (FIG. 5a). Increased microvascular leakage and hypervascularity had been previously demonstrated in homozygous K14-VEGF164 transgenic mice (Thurston, G., C. Suri, K. Smith, J. McClain, T. Sato, G. Yancopoulos, and D. McDonald. 1999. *Science* 286: 2511–2514). However, a projected four-fold elevation of VEGF mRNA expression extrapolated from the data from the heterozygous K14-VEGF164 transgenic mice would still fail to approximate the marked induction of total VEGF mRNA in the K14-HIF-1αΔODD transgenic mice.

Figure 5B:
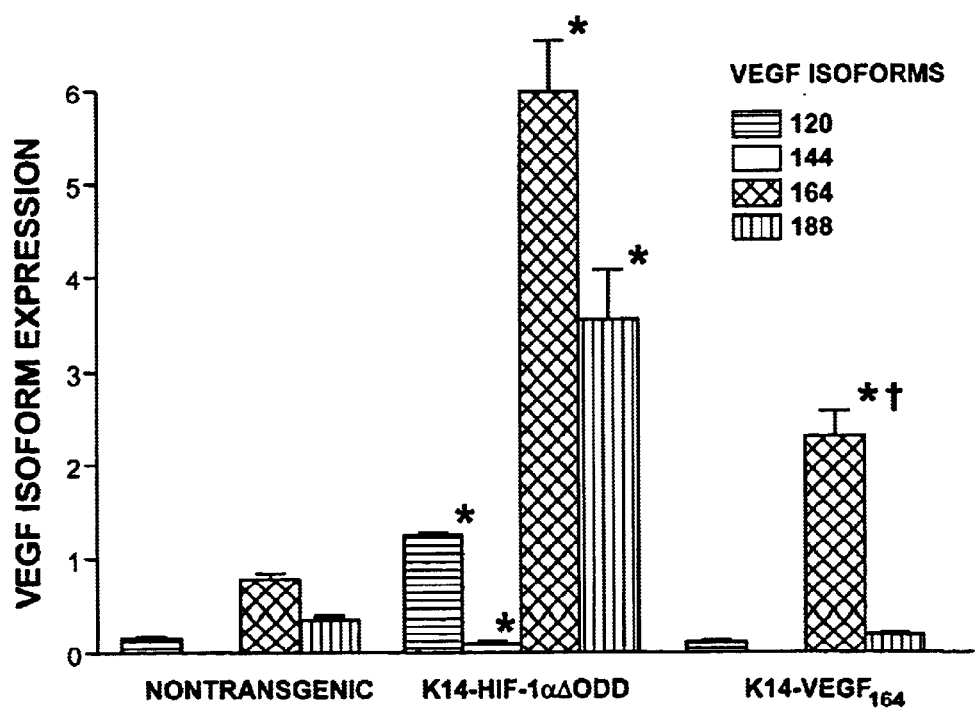
Figure 5C:
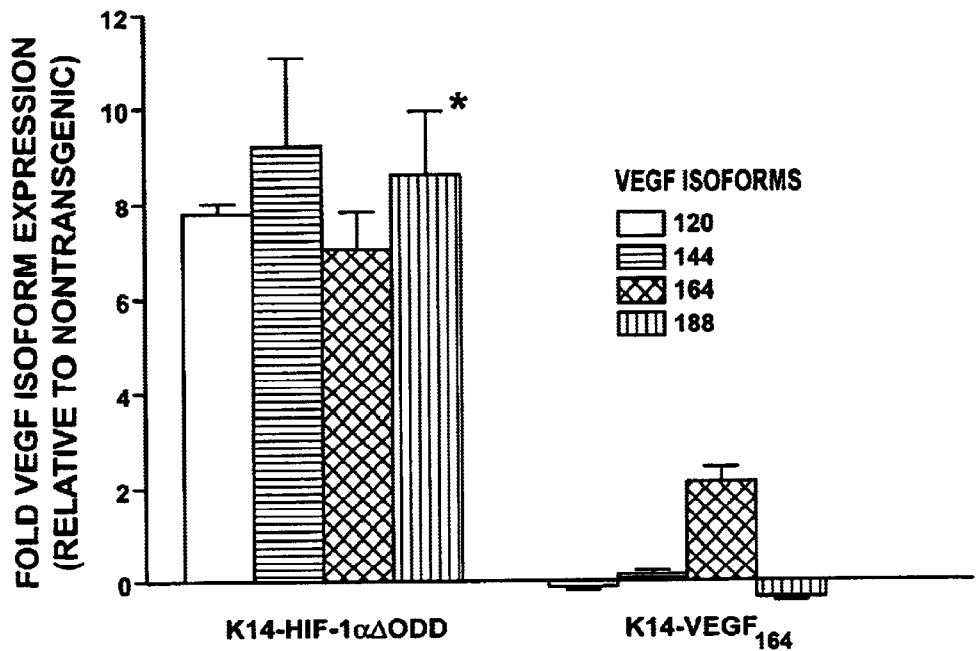
Figure 5D:
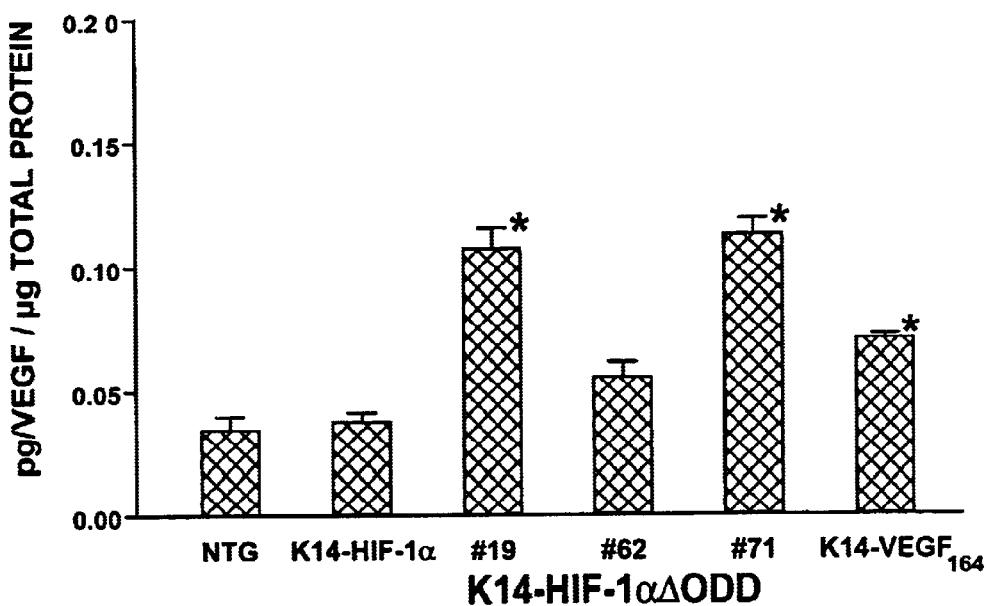

Whether the marked induction of VEGF mRNA due to gain of HIF-1α function was also present at the level of protein was also investigated. Ear extracts from HIF-1α, HIF-1αΔODD, and VEGF164 transgenic and non-transgenic controls were analyzed by ELISA (FIG. 5d). Approximately one quarter of one ear from each mouse was clipped and snap frozen, then homogenized on ice at high speed for 1 min. in 200–300 μl RIPA buffer (150 mM NaCl, 1% NP-40, 0.5% DOC, 0.1% SDS, 50 mM Tris, pH 8.0) containing 1×Complete Mini Protease Inhibitors (Roche, Indianapolis, Ind.) and 0.5 mM EDTA. Extracts were incubated on ice for at least 30 min. with occasional vortexing and centrifuged at 14,000 rpm for 10 minutes. Supernatants were reserved and protein concentrations were determined with the DC Protein Assay (BioRad, Hercules, Calif.). VEGF content of 10 μg total protein was determined using the Quantikine M kit (R & D Systems, MInneapolis, Minn.) according to manufacturer's instructions. Plates were read and analyzed on a SPECTRAmax 340 running SOFTmax PRO 3.1.1 (Molecular Devices, Sunnyvale, Calif.).

K14-HIF-1αΔODD transgenic mice demonstrated a 3-fold induction of VEGF protein expression in the two of the three lines (#'s 19 and 71), compared to either K14-HIF-1α or non-transgenic mice (FIG. 5d). Heterozygous K14-VEGF164 transgenic mice displayed a 2-fold induction of VEGF protein compared to controls (FIG. 5d). These protein levels are likely to underestimate local VEGF concentrations adjacent to transgenic keratinocytes since the whole ear, including dermis, muscle, and cartilage, was homogenized. This level of VEGF protein induction is similar to that reported from ischemic hearts or brains (Banai et al. 1994; Lee et al. 1999; Lee et al. 2000b; Miraliakbari et al. 2000). Thus, inadequate induction of VEGF mRNA or VEGF protein does not explain the lack of baseline leak mediated by HIF-1αΔODD overexpression.

Five isoforms are expressed from the VEGF-A gene (Tober, K., et al. 1998. Biochemical and Biophysical Research Communications 247: 644–653), and it is becoming increasingly apparent that different VEGF isoforms mediate distinct facets of vascular biology (Cheng, S. et al. *Proceedings of the National Academy of Sciences of the United States of America* 94: 12081–12087) (Carmeliet, P. et al. 1999. *Nature Medicine* 5: 495–502) (Grunstein, J. et al. *Molecular and Cellular Biology* 20: 7282–7291). As such, an alternative explanation for disparity in vascular leakage was that the composition of VEGF isoform expression was different in the K14-HIF-1αΔODD and the K14-VEGF164 groups. Thus, the expression profile of the four most abundant VEGF isoforms (Tober, K., et al. 1998. Biochemical and Biophysical Research Communications 247: 644–653) was determined in ear skin from K14-HIF-1αΔODD and heterozygous K14VEGF164 transgenic mice, and non-transgenic controls. Real-time RT-PCR with isoform-specific flanking primers and TaqMan probes complementary to the unique splice junctions of VEGF120, 144, 164, and 188 were used (FIG. 5b). Histone 3.3A expression was used as a reference.

In non-transgenic mice, VEGF164 was expressed at the highest level (FIG. 5b). VEGF188 was expressed at 50%, VEGF120 at 19% and VEGF144 at 1.0% of the level of VEGF164. The expression level of each VEGF isoform was significantly elevated in the K14-HIF-1αΔODD transgenic mice compared to non-transgenic controls (FIG. 5b). However, the pattern of isoform expression in K14-HIF-1αΔODD transgenic mice was not statistically different from non-transgenic controls (FIG. 5b). Calculation of the fold-induction of VEGF expression relative to non-transgenic controls revealed an equivalent 7 to 9-fold elevation of each of the VEGF isoforms from ear skin of K14-HIF-1α∆ODD transgenic mice (FIG. 5c). In contrast, VEGF164 was the only isoform whose expression was significantly increased compared to non-transgenic controls in the K14-VEGF164 transgenic mice (FIGS. 5b and 5c). Moreover, the 2-fold elevation of the VEGF164 isoform here, compared to a similar fold-induction in the previous analysis of total VEGF expression (FIG. 5a), both internally validates the real-time RT-PCR techniques, and also underscores the sole elevation of the 164 isoform in this transgenic model. A "balanced" induction of each VEGF isoform may be in part responsible for development of a non-leaky microvasculature in response to HIF-1α overexpression.

Example 8
Acceleration of Wound Healing in Mice Expressing a Stable HIF-1α Variant Full thickness wounds were created in non-transgenic mice, K14-HIF-1α∆ODD transgenic mice and K-14-HIF-1α transgenic mice, according to the methods described in Elson et al. (2000. Cancer Res. 60: 6189–6195), which is hereby incorporated by reference. Briefly, 1.5×1.5 cm, full-thickness back wounds were created and covered with a sterile dressing and then serially harvested at various time points. Wound healing was established based on the rate of reepithelization as assessed using hematoxylin and eosin staining.

Figure 8:
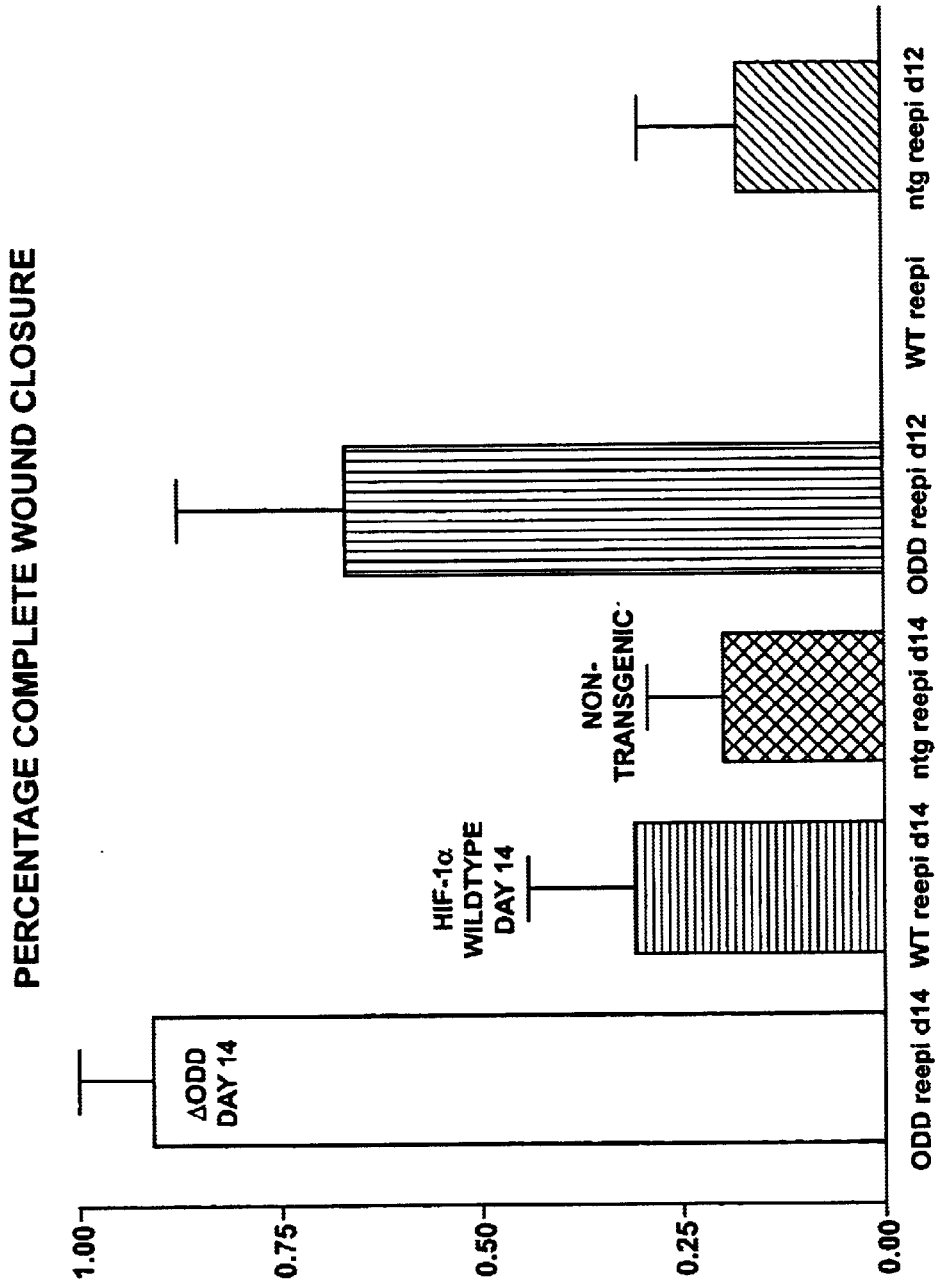
FIG. 8 Acceleration of Wound Healing in K14-HIF-1αΔODD Mice The rate of reepithelilization was measured in K14-HIF-1αΔODD transgenic mice (ΔODD), K14-HIF-1α transgenic mice (wild type) and non-transgenic mice following the creation of full thickness wounds. Wound healing was accelerated in mice expressing stable HIF-1α variant HIF-1αΔODD.

After 12 days, less than 25% of non-transgenic (ntg) mice showed complete wound closure (FIG. 8). In contrast, approximately 75% of transgenic mice expressing HIF-1α∆DD showed wound closure (FIG. 8). Specifically, at day 12 4 of 6 K14-HIF1α∆ODD mice were completely reepithelialized compared to 2 of 11 nTg mice.

After 14 days, 16 K14-HIF1α-∆ODD transgenic mice and 20 non-transgenic (nTg) mice were harvested. While there was no difference in the rate of wound contracture, 15 of 16 K14-HIF1α-∆ODD mice had complete reepithelialization by day 14 (FIG. 8). In contrast only 4 of 20 non-transgenic mice and 4 of 13 wild-type HIF-1α mice were completely reepithelialized at day 14 (FIG. 8).

Epithelial maturation was then investigated using immunohistochemistry for keratin 10 (K10) expression in the new epithelium. K14-HIF1α-∆ODD had earlier K10 expression with 5 of 11 mice expressing K10 in the central portion of the wound compared to 0 of 21 nTg mice. Blood vessel analysis using IHC for CD31 suggests an accelerated maturation of the dermis, with earlier resolution of the brisk dermal angiogenesis characteristic of wound granulation tissue.

Although the present invention has been described in detail, it is understood that various modifications can be made without departing from the spirit of the invention. Accordingly, the invention is limited only by the following claims. All cited patents, patent applications and publications referred to in this application are herein incorporated by reference in their entirety.

What is claimed is:

1. A method of accelerating wound healing in a mammal comprising administering to the mammal a stable variant of an hypoxia inducible factor-1α (HIF-1α) polypeptide, wherein said polypeptide comprises amino acids 1-400 of SEQ ID NO: 2 and comprises an insertion, substitution, or deletion within an oxygen-dependent degradation domain (ODD), said ODD comprising amino acids 401–603 of SEQ ID NO: 4.

2. The method of claim 1, wherein the stable variant comprises, a substitution or deletion within the ODD.

3. The method of claim 2, wherein the stable variant comprises an additional insertion, substitution or deletion outside of the ODD.

4. The method of claim 2, wherein the stable variant comprises a deletion within the ODD.

5. The method of claim 4, wherein the stable variant comprises the amino acid sequence of SEQ ID NO: 2.

6. The method of claim 1, wherein the stable variant comprises a functional HIF-1α transactivation domain.

7. The method of claim 1, wherein the stable variant comprises a heterologous transactivation domain.

8. The method of claim 1, wherein the mammal is human.

9. The method of claim 1, wherein the mammal is a domesticated animal.

10. The method of claim 1, wherein the administration is topical.

11. The method of claim 1, wherein the administration is directly to the wound.

12. The method of claim 1, wherein said wound is caused by mechanical, chemical or thermal trauma.

13. The method of claim 12, wherein the wound is the result of a surgical incision.

14. The method of claim 12, wherein said wound is selected from the group consisting of a contusion, an incision and a laceration.

15. The method of claim 1, wherein the wound is associated with a disease or disorder.

16. The method of claim 1, additionally comprising administering a growth factor to the mammal.

17. The method of claim 16, wherein said growth factor is selected from the group consisting of vascular endothelial growth factor (VEGF) and fibroblast growth factor (FGF).

18. The method of claim 17, wherein said growth factor is VEGF.

19. A pharmaceutical composition comprising a stable HIF-1α variant polypeptide according to claim 1 in association with a pharmaceutically acceptable carrier.

20. The pharmaceutical composition of claim 19 which is suitable for topical delivery.

21. The pharmaceutical composition of claim 20 which is an ointment, cream or gel.

22. The pharmaceutical composition of claim 19 which is suitable for systemic delivery.

23. A method of accelerating wound healing in a mammal comprising administering to the mammal a stable variant of an hypoxia-inducible factor-1α (HIF-1α) polypeptide, wherein said polypeptide comprises an insertion, substitution, or deletion within the [an] oxygen-dependent degradation domain (ODD), wherein the wound is associated with diabetes.

24. The method of claim 23, wherein the wound is a diabetic ulcer.

* * * * *